United States Patent
Heartlein et al.

(10) Patent No.: US 11,224,642 B2
(45) Date of Patent: *Jan. 18, 2022

(54) MRNA THERAPY FOR ARGININOSUCCINATE SYNTHETASE DEFICIENCY

(71) Applicant: TRANSLATE BIO, INC., Cambridge, MA (US)

(72) Inventors: Michael Heartlein, Lexington, MA (US); Frank DeRosa, Lexington, MA (US); Lianne Smith, Lexington, MA (US)

(73) Assignee: Translate Bio, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/521,351

(22) Filed: Oct. 22, 2014

(65) Prior Publication Data

US 2015/0110859 A1 Apr. 23, 2015

Related U.S. Application Data

(60) Provisional application No. 61/894,294, filed on Oct. 22, 2013.

(51) Int. Cl.
| | |
|---|---|
| A61K 31/7088 | (2006.01) |
| A61K 9/127 | (2006.01) |
| A61K 38/53 | (2006.01) |
| C12N 9/00 | (2006.01) |
| A61K 48/00 | (2006.01) |
| A61K 9/51 | (2006.01) |
| A61K 31/7105 | (2006.01) |

(52) U.S. Cl.
CPC ............ *A61K 38/53* (2013.01); *A61K 9/1272* (2013.01); *A61K 9/5123* (2013.01); *A61K 31/7105* (2013.01); *C12N 9/93* (2013.01); *C12Y 603/04005* (2013.01); *A61K 48/00* (2013.01); *A61K 48/005* (2013.01)

(58) Field of Classification Search
None
See application file for complete search history.

(56) References Cited

U.S. PATENT DOCUMENTS

| | | | |
|---|---|---|---|
| 2,647,121 A | 7/1953 | Jacoby | |
| 2,717,909 A | 9/1955 | Kosmin | |
| 2,819,718 A | 1/1958 | Goldman | |
| 2,844,629 A | 7/1958 | William et al. | |
| 3,096,560 A | 7/1963 | Liebig | |
| 3,535,289 A | 10/1970 | Yoshihara et al. | |
| 3,614,954 A | 10/1971 | Mirowski et al. | |
| 3,614,955 A | 10/1971 | Mirowski | |
| 3,656,185 A | 4/1972 | Carpentier | |
| 3,805,301 A | 4/1974 | Liebig | |
| 3,945,052 A | 3/1976 | Liebig | |
| 3,995,623 A | 12/1976 | Blake et al. | |
| 4,013,507 A | 3/1977 | Rembaum | |
| 4,072,146 A | 2/1978 | Howes | |
| 4,096,860 A | 6/1978 | McLaughlin | |
| 4,099,528 A | 7/1978 | Sorenson et al. | |
| 4,106,129 A | 8/1978 | Carpentier et al. | |
| 4,134,402 A | 1/1979 | Mahurkar | |
| 4,140,126 A | 2/1979 | Choudhury | |
| 4,180,068 A | 12/1979 | Jacobsen et al. | |
| 4,182,833 A | 1/1980 | Hicks | |
| 4,227,533 A | 10/1980 | Godfrey | |
| 4,284,459 A | 8/1981 | Patel et al. | |
| 4,308,085 A | 12/1981 | Horhold et al. | |
| 4,323,525 A | 4/1982 | Bornat | |
| 4,335,723 A | 6/1982 | Patel | |
| 4,339,369 A | 7/1982 | Hicks et al. | |
| 4,355,426 A | 10/1982 | MacGregor | |
| 4,375,817 A | 3/1983 | Engle et al. | |
| 4,385,631 A | 5/1983 | Uthmann | |
| 4,401,472 A | 8/1983 | Gerber | |
| 4,406,656 A | 9/1983 | Hattler et al. | |
| 4,475,972 A | 10/1984 | Wong | |

(Continued)

FOREIGN PATENT DOCUMENTS

| | | |
|---|---|---|
| CA | 2518132 A1 | 3/2006 |
| CA | 2807552 A1 | 2/2012 |

(Continued)

OTHER PUBLICATIONS

Chandler et al, Liver-directed adeno-associated virus serotype 8 gene transfer rescues a lethal murine model of citrullinemia type 1, Gene Therapy (2013) 20, 1188-1191.*
McIvor, Therapeutic Delivery of mRNA: The Medium Is the Message, Molecular Therapy, 2011, pp. 822-823.*
Fath et al, Multiparameter RNA and Codon Optimization: A Standardized Tool to Assess and Enhance Autologous Mammalian Gene Expression, PLoS One, 2011, vol. 6(3), pp. 1-14.*
Sahin et al, mRNA-based therapeutics—developing a new class of drugs, Nature reviews, 2014, pp. 759-780.*
Balachandran S. et al., Essential role for the dsRNA-dependent protein kinase PKR in innate immunity to viral infection, Immunity 13, 129-141 (2000).*

(Continued)

*Primary Examiner* — Maria Marvich
(74) *Attorney, Agent, or Firm* — Proskauer Rose LLP; Fangli Chen

(57) ABSTRACT

The present invention provides, among other things, methods of treating Argininosuccinate Synthetase Deficiency (ASD), including administering to a subject in need of treatment a composition comprising an mRNA encoding argininosuccinate synthetase (ASS1) at an effective dose and an administration interval such that at least one symptom or feature of ASD is reduced in intensity, severity, or frequency or has delayed in onset. In some embodiments, the mRNA is encapsulated in a liposome comprising one or more cationic lipids, one or more non-cationic lipids, one or more cholesterol-based lipids and one or more PEG-modified lipids.

16 Claims, 11 Drawing Sheets

Specification includes a Sequence Listing.

(56) References Cited

U.S. PATENT DOCUMENTS

| | | |
|---|---|---|
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,450,298 B2 | 5/2013 | Mahon et al. |
| 8,450,467 B2 | 5/2013 | Manoharan et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |

(56) References Cited

U.S. PATENT DOCUMENTS

| | | |
|---|---|---|
| 8,710,200 B2 | 4/2014 | Schrum et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,005,930 B2 | 4/2015 | Jendrisak et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,040,256 B2 | 5/2015 | Grunenwald et al. |
| 9,051,567 B2 | 6/2015 | Fitzgerald et al. |
| 9,061,021 B2 | 6/2015 | Guild et al. |
| 9,061,059 B2 | 6/2015 | Chakraborty et al. |
| 9,074,208 B2 | 7/2015 | MacLachlan et al. |
| 9,080,211 B2 | 7/2015 | Grunenwald et al. |
| 9,085,801 B2 | 7/2015 | Grunenwald et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,428,751 B2 | 8/2016 | MacDonald et al. |
| 9,464,124 B2 | 10/2016 | Bancel et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0181410 A1 | 9/2003 | Wheeler et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0142025 A1 | 7/2004 | MacLachlan et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2007/0135372 A1 | 6/2007 | MacLachlan et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0331234 A1 | 12/2010 | Mahon et al. |
| 2011/0009641 A1 | 1/2011 | Anderson et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2011/0287435 A1 | 11/2011 | Grunenwald et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0017223 A1 | 1/2013 | Hope et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |

(56) References Cited

U.S. PATENT DOCUMENTS

| | | |
|---|---|---|
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0111248 A1 | 4/2015 | Bancel et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0191760 A1 | 7/2015 | Jendrisak et al. |
| 2015/0265708 A1 | 9/2015 | Manoharan et al. |
| 2015/0267192 A1 | 9/2015 | Heartlein et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0264971 A1 | 9/2016 | Geisbert et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |

FOREIGN PATENT DOCUMENTS

| | | |
|---|---|---|
| CA | 2807 552 | 9/2012 |
| CN | 100569877 C | 12/2009 |
| CN | 101863544 A | 10/2010 |
| DE | 24 30 998 A1 | 1/1975 |
| DE | 2520814 A1 | 11/1976 |
| DE | 3728917 A1 | 3/1989 |
| EP | 6 73 637 A1 | 9/1995 |
| EP | 0783297 A1 | 7/1997 |
| EP | 0853123 A1 | 7/1998 |
| EP | 0959092 A1 | 11/1999 |
| EP | 2449106 A1 | 11/1999 |
| EP | 1519714 B1 | 4/2005 |
| EP | 2045251 A1 | 4/2009 |
| EP | 1519 714 | 10/2010 |
| EP | 2338478 B1 | 6/2011 |
| EP | 2449 106 | 5/2012 |
| EP | 2532649 A1 | 12/2012 |
| EP | 2578685 A2 | 4/2013 |
| EP | 2823 809 | 1/2015 |
| EP | 2823809 A1 | 1/2015 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 50-24216 B2 | 9/2012 |
| WO | WO-90/11092 A1 | 10/1990 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-1998/010748 A1 | 3/1998 |
| WO | WO-98/16202 A2 | 4/1998 |
| WO | WO-98/51278 A2 | 11/1998 |
| WO | WO-99/14346 A2 | 3/1999 |
| WO | WO-00/03044 A1 | 1/2000 |
| WO | WO-00/062813 A2 | 10/2000 |

(56) References Cited

FOREIGN PATENT DOCUMENTS

| | | |
|---|---|---|
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/22709 A1 | 3/2002 |
| WO | WO-02/31025 A2 | 4/2002 |
| WO | WO-02/42317 A2 | 5/2002 |
| WO | WO-2002/34236 A2 | 5/2002 |
| WO | WO-03/040288 A2 | 5/2003 |
| WO | WO-03/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO2005/026372 | 3/2005 |
| WO | WO-2005/026372 A1 | 3/2005 |
| WO | WO-2005/028619 A2 | 3/2005 |
| WO | WO-2005/037226 A2 | 4/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/045548 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/127060 A1 | 10/2009 |
| WO | WO-2009/127230 A1 | 10/2009 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A2 | 3/2013 |
| WO | WO-2013/063468 A1 | 5/2013 |
| WO | WO2013/090186 | 6/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/182683 A1 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO2014/113089 | 7/2014 |
| WO | WO-2014/113089 A2 | 7/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | 2015006747 A2 | 1/2015 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO2015/085318 | 6/2015 |
| WO | WO2015/089511 | 6/2015 |
| WO | WO2015/011633 | 1/2016 |
| WO | 2016054421 A1 | 4/2016 |
| WO | WO2016/054421 | 4/2016 |
| WO | 2016071857 A1 | 5/2016 |
| WO | 2016077123 A1 | 5/2016 |
| WO | 2016077125 A1 | 5/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |

OTHER PUBLICATIONS

Sercombe et al, Advances and Challenges of Liposome Assisted Drug Delivery, Front. Pharmacol. 6:286, 2015, pp. 1-13.*
Saffari et al, Barriers to Liposomal Gene Delivery: from Application Site to the Target, Iranian Journal of Pharmaceutical Research (2016), 15 (Special issue): 3-17.*
Hackman, DG, Translating animal research into clinical benefit, BMJ, 2007, pp. 163-168.*
Martinez, M.N., Factors Influencing the Use and Interpretation of Animal Models in the Development of Parenteral Drug Delivery Systems, The AAPS Journal, vol. 13, No. 4, Dec. 2011, p. 632-649.*
Kaczmarek et al., Advances in the delivery of RNA therapeutics: from concept to clinical reality, Genome Medicine (2017) 9:60, pp. 1-16.*
Carlsson et al, Biocompatible, Purified VEGF-A mRNA Improves Cardiac Function after Intracardiac Injection 1 Week Post-

(56) References Cited

OTHER PUBLICATIONS myocardial Infarction in Swine, Molecular Therapy: Methods & Clinical Development vol. 9 Jun. 2018, pp. 330-346.*
U.S. Appl. No. 60/083,294.
Alton et al., Cationic Lipid-Mediated CFTR Gene Transfer to the Lungs and Nose of Patients with Cystic Fibrosis: a Double-Blind Placebo-Controlled Trial, Lancet, 353: 947-954 (1999).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Andries et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Not Known, Oligotex Handbook, Qiagen (2002).
Author Not Known, PolyATtract mRNA Iosaltion Systems, Promega (2012).
Barreau, C. et al., Liposome-mediated RNA transfection should be used with caution, RNA, 12:1790-1793 (2006).
Behr et al.. Efficient Gene Transfer into Mammalian Primary Endocrine Cells with Lipo Polyamine-Coated DNA, Proc. Nat.'l Acad. Sci., 86: 6982-6986 (1989).
Bloomfield, V.A., Quasi-Elastic Light Scattering Applications in Biochemistry and Biology, Ann. Rev. Biophys. Bioeng. 10:421-450 (1981).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Chiou, H.C. et al., Enhanced resistance to nuclease degradation of nucleic acids complexed to; asialoglycoprotein-polylysine carriers, Nucleic Acids Research, 22(24):5439-46 (1994).
Conese et al., Gene and Cell Therapy for Cystic Fibrosis: From Bench to Bedside, J. Cyst. Fibros., 10 Suppl 2: S114-s128 (2011).
Cowling, V.H., Regulation of mRNA cap methylation, Biochemical Journal, 425:295-302 (2010).
Dande, P. et al., Improving RNA interference in mammalian cells by 4'-thio-modified small interfering RNA (siRNA): effect on siRNA activity and muclease stability when used in combination with 2'-0-alkyl modifications, Journal of Medicinal Chemistry, 49(5): 1624-1634 (2006).
Debus et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148: 334-343 (2010).
Demeshkina, N. et al., Interactions of the ribosome with mRNA and tRNA, Current Opinion in Structural Biology, 20(3):325-332 (2010).
Dong, Y. et al., Lipopeptide nanoparticles for potent and selective siRNA delivery in rodents and nonhuman primates, Proceedings of the National Academy of Sciences, 111(11): 3955-3960 (2014).
Drummond, D.C. et al., Optimizing Liposomes for Delivery of Chemotherapeutic Agents to Solid Tumors, Pharmacological Reviews, 51(4): 691-743 (1999).
Elton, C., The Next Next Big Thing, Boston Magazine, pp. 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst et al., Interaction of Liposomal and Polycationic Transfection Complexes with Pulmonary Surfactant, J. Gene. Med., 1: 331-340 (1999).

Estimated No. of Animal and Plant Species on Earth, http://www.factmonster.com/ipka/A0934288.html, 2000-2014, 3 pages, (Retreived Aug. 2, 2014).
Fechter, P. et al., Recognition of mRNA cap structures by viral and cellular proteins, Journal of General Virology, 86:1239-1249 (2005).
Felgner et al., Lipofection: A Highly Efficient, Lipid-Mediated DNA-Transfection Procedure, Proc. Natl. Acad., 84:7413-7417 (1987).
Felgner, P.L. and Ringold, G.M., Cationic liposome-mediated transfection, Nature, 337(6205):387-388 (1989).
Fernandez, V. et al., Cross Flow Filtration of RNA Extracts by Hollow Fiber Membrane, Acta Biotechnologica, 12(1):49-56 (1992).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-92 (2004).
Fumoto et al., Targeted Gene Delivery: Importance of Administration Routes, Novel Gene Therapy Approaches, Mar. 31, 2013.
Galipon, J. et al., Stress-induced lncRNAs evade nuclear degradation and enter the translational machinery, Genes to Cells, 18(5):353-368 (2013).
Gao, X. et al., A novel cationic liposome reagent for efficient transfection of mammalian cells, Biochemical and Biophysical Research Communications, 179(1):280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grudzien, E. et al., Novel cap analogs for in vitro synthesis of mRNAs with high translational efficiency, RNA Biology, 10(9):1479-1487 (2004).
Guttman, M. et al., Chromatin signature reveals over a thousand highly conserved large non-coding RNAs in mammals, Nature, 458:223-227 (2009).
Harada-Shiba, M. et al., Polyion complex micelles as vectors in gene therapy—pharmacokinetics and in vivo; gene transfer, Gene Therapy, 9(6):407-14 (2002).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Hess et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy: CII, 55(6): 672-83 (2006).
Heyes et al., Cationic Lipid Saturation Influences Intracellular Delivery of Encapsulated Nucleic Acids, J. Controlled Release, 107: 276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hillery, A.M. et al., Drug Delivery and Targeting for Pharmacists and Pharmaceutical Scientists, Taylor and Francis (2005).
Hoerr et al., In Vivo Application of RNA Leads to Induction of Specific Cytotoxic T Lymphocytes and Antibodies, European Journal of Immunology, 30(1): 1-7 (2000).

(56) References Cited

OTHER PUBLICATIONS

Hope, M.J. et al., Reduction of Liposome Size and Preparation of Unilamellar Vesicles by Extrusion Techniques, In: Liposome Technology, 1:123-139 (1993).

Horwich, A.L. et al., Structure and Expression of a Complementary DNA for the Nuclear Coded Precursor of Human Mitochondrial Ornithine Transcarbamylase, Science, 224(4653):1068-1074 (1984).

Horwich, A.L. et al., Targeting of Pre-Ornithine Transcarbamylase to Mitochondria: Definition of Critical Regions and Residues in the Leader Peptide, Cell, 44:451-459 (1986).

Huang, Z. et al., Thiocholesterol-based lipids for ordered assembly of bioresponsive gene carriers, Molecular Therapy, 11(3):409-417 (2005).

Huttenhofer, A. and Noller, H., Footprinting mRNA-ribosome complexes with chemical probes, The EMBO Journal, 13(16):3892-3901 (1994).

Jakobsen, K. et al., Purification of MRNA Directly From Crude Plant Tissues in 15 Minutes Using Magnetic Oligo DT Microsheres, Nucleic Acids Research, 18(12):3669 (1990).

Jeffs, L.B. et al., A scalable, extrusion-free method for efficient liposomal encapsulation of plasmid DNA, Pharmaceutical Research, 22(3):362-372 (2005).

Jones, G. et al., Duplex- and Triplex-Forming Properties of 4'-Thio-Modified Oligodeoxynucleotides, Bioorganic & Medicinal Chemistry Letters, 7(10):1275-1278 (1997).

Kariko, K. et al., In vivo protein expression from mRNA delivered into adult rat brain, Journal of Neuroscience Methods, 105(1):77-86 (2001).

Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).

Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).

Kiew, L.V. et al., Effect of antisense oligodeoxynucleotides for ICAM-1 on renal ischaemia-reperfusion injury in the anaesthetised rat, The Journal of Physiology, 557(3):981-989 (2004).

Klibanov, A.L. et al., Amphipathic polyethyleneglycols effectively prolong the circulation time of liposomes, FEBS, 268(1): 235-237 (1990).

Kober et al., Optimized Signal Peptides for the Development of High Expressing CHO Cell Lines, Biotechnol. Bioeng., 110: 1164-1173 (2012).

Kormann, M.S.D. et al., Expression of therapeutic proteins after delivery of chemically modified mRNA in mice, Nature Biotechnology, 29(2):154-157 (2011).

Kozak, M. An analysis of 5'-noncoding sequences from 699 vertebrate messenger RNAs, Nucleic Acid Research, 15(20):8125-8148 (1987).

Krieg, P.A. et al., In vitro RNA synthesis with SP6 RNA polymerase, Methods in Enzymology, 155:397-415(1987).

Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).

Lam, J.K.W et al., Pulmonary delivery of therapeutic siRNA, Advanced Drug Delivery Reviews (2011).

Lasic, D.D. et al., Gelation of liposome interior: A novel method for drug encapsulation, FEBS, 312(2,3):255-258 (1992).

Lasic, D.D. Novel applications of liposomes, Trends in Biotechnology, 16:307-321 (1998).

Li, L. et al., Preparation and Gene Delivery of Alkaline Amino Acids-Based Cationic Liposomes, Archives of Pharmaceutical Research, 31(7):924-931 (2008).

Li, S. et al., In vivo gene transfer via intravenous administration of cationic lipid-protamine-DNA (LPD) complexes, Gene Therapy, 4:891-900 (1997).

Li, W. et al., Lipid-based Nanoparticles for Nucleic Acid Delivery, Pharmaceutical Research, 24(3):438-449 (2007).

Liebhaber, S.A. et al., Translation inhibition by an mRNA coding region secondary structure is determined by its proximity to the AUG initiation codon, Journal of Molecular Biology, 226(3):609-621 (1992).

Lindgren, V. et al., Human Ornithine Transcarbamylase Locus Mapped to Band Xp21.1 Near the Duchenne Muscular Dystrophy Locus, Science, 226(2675):698-700 (1984).

Liu et al., COStar: a D-star Lite-based Dynamic Search Algorithm for Codon Optimization, Journal of Theoretical Biology, 344: 19-30 (2014).

Liu, Y. et al., Designer Lipids Advance Systemic siRNA Delivery, Molecular Therapy, 18(4):669-670 (2010).

Lo, K-M et al., High level expression and secretion of Fc-X fusion proteins in mammalian cells, Protein Engineering, 11(6)495-500 (1998).

Love, K.T. et al., Lipid-like materials for low-dose, in vivo gene silencing, PNAS, 107(5):1864-1869 (2010).

Lu, D. et al., Optimization of methods to achieve mRNA-mediated transfection of tumor cells in vitro and in vivo employing cationic liposome vectors, Cancer Gene Therapy, 1(4):245-52 (1994).

Maclachlan, I. et al., Lipid nanoparticle-mediated delivery of messenger RNA, 1st International mRNA health conference, Tubingen, Germarny (2013).

Maeda-Mamiya, R. et al.,. In vivo gene delivery by cationic tetraamino; fullerene. Proceedings of National Academy of Sciences U S A, 107(12):5339-44 (2010).

Malone, R.W., et al., Cationic liposome-mediated RNA transfection, PNAS, 86:6077-6081 (1989).

Mammal, http://en.wikipedia.org/wiki/Mammal, 2007, Pearson Education, NY, NY, Author unkown (Source: The international union for conservation of nature and natural resources), 2 pages, (Retreived Aug. 2, 2014).

Mansour, H.M. et al., Nanomedicine in pulmonary delivery, International Journal of Nanomedicine, 4:299-319 (2009).

Martinon et al., Induction of Virus-Specific Cytotoxic T Lymphocytes in Vivo by Liposome-Entrapped mRNA, European Journal of Immunology, 23(7): 1719-22 (1993).

Mccracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).

Melton, D.A. et al., Efficient in vitro synthesis of biologically active RNA and RNA hybridization probes from; plasmids containing a bacteriophage SP6 promoter, Nucleic Acids Research, 12(18):7035-56 (1984).

Merkel, O.M. et al., Nonviral Pulmonary Delivery of siRNA, Accounts of Chemical Research, 10 pages (2011).

Merten, O. et al., Large-Scale Manufacture and Characterizationof a Lentiviral Vector Produced for Clinical Ex Vivo Gene Therapy Application, Human Gene Therapy, 22(3):343-356 (2011).

Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).

Morrissey et al., Potent and Persistent in vivo Anti-HBV Activity of Chemically Modified siRNAs, Nat. Biotechnol., 23(8): 1003-1007 (2005).

Ng, J. et al., LincRNAs join the pluripotency alliance, Nature Genetics, 42:1035-1036 (2010).

Nojima, T. et al., The Interaction between Cap-binding Complex and RNA Export Factor is Required for Intronless mRNA Export, Journal of Biological Chemistry, 282(21):15645-15651 (2007).

Okumura, K. et al., Bax mRNA therapy using cationic liposomes for human malignant melanoma, The Journal of Gene Medicine, 10:910-917 (2008).

Otsuka, Y. et al., Identification of a Cytoplasmic Complex That Adds a Cap onto 5'-Monophosphate RNA, Molecular and Cellular Biology, 29(8):2155-2167 (2009).

Painter et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.

(56) References Cited

OTHER PUBLICATIONS

Painter et al., Topical Delivery of mRNA to the Murine Lung and Nasal Epithelium, Molecular Therapy, 9: S187 (2004).
Painter, An Investigation of mRNA as a Gene Transfer Agent, Oxford University GeneMedicine, Abstract Only, 1 page (2007).
Probst, J. et al., Spontaneous cellular uptake of exogenous messenger RNA in vivo is nucleic acid-specific, saturable and ion dependent, Gene Therapy, 14:1175-1180 (2007).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Reddy, A. et al., The Effect of Labour and Placental Separation on the Shedding of Syncytiotrophoblast Microparticles, Cell-free DNA and mRNA in Normal Pregnancy and Preeclampsia, Placenta, 29:942-949.
Rejman, J. et al., Characterization and transfection properties of lipoplexes stabilized with novel exchangeable polyethylene glycol-lipid conjugates, Biochimica et Biophysica Acta, 1660:41-52 (2004).
Rosenecker et al., Gene Therapy for Cystic Fibrosis Lung Disease: Current Status and Future Perspectives, Curr. Opin. Mol. Ther., 8: 439-445 (2006).
Rosenecker et al., Interaction of Bronchoalveolar Lavage Fluid with Polyplexes and Lipoplexes: Analysing the Role of Proteins and Glycoproteins, J. Gene. Med., 5: 49-60 (2003).
Rowe et al., Cystic Fibrosis, New Engl. J. Med. 352: 1992-2001 (2005).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, Han, The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shimada, A. et al., Translocation Pathway of the Intratracheally Instilled Ultrafine Particles from the Lung into the Blood Circulation in the Mouse, Toxicologic Pathology, 34:949-957 (2006).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Su, X. et al., In Vitro and in Vivo mRNA Delivery Using Lipid-Enveloped pH-Responsive Polymer Nanopartides, Molecular Pharmaceutics, 8(3):774-787 (2011).
Tagawa, M. et al., Gene expression and active virus replication in the liver after injection of duck hepatitis B virus DNA into the peripheral vein of ducklings, Journal of Hepatology, 24:328-334 (1996).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tavernier, G. et al., mRNA as gene therapeutic: How to control protein expression, Journal of Controlled Release, 150:238-247 (2011).
Tsui, N.B. et al., Stability of endogenous and added RNA in blood specimens, serum, and plasma, Clinical Chemistry, 48(10): 1647-53 (2002).
Tuschl, T. et al., Targeted mRNA degradation by double-stranded RNA in vitro, Genes and Development, 13(24):3191-7 (1999).
Van Der Gun, B.T.F et al., Serum insensitive, intranuclear protein delivery by the multipurpose cationic lipid Saint-2, Journal of Controlled Release, 123:228-238 (2007).

Van Tendeloo, V.F.I et al., mRNA-based gene transfer as a tool for gene and cell therapy, Current Opinion in Molecular Therapeutics, 9(5):423-431 (2007).
Varambally, S. et al., Genomic Loss of microRNA-101 Leads to Overexpression of Histone Methyltransferase EZH2 in Cancer, Science, 322:1695-1699 (2008).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicirde-DNA vector, Human Gene Therapy, 23(10):A145 (2012).
Viecelli, H. et al., Gene therapy for liver diseases using non-viral minicircle-DNA vector, Molecular Therapy, 21 (1):S136 (2013).
Vomelova, I. et al., Methods of RNA Purification. All Ways (Should) Lead to Rome, Folia Biologica, 55(6):242-251 (2009).
Wang, H. et al., N-acetylgalactosamine functionalized mixed micellar nanoparticles for targeted delivery of siRNA to liver, Journal of Controlled Release, 166(2):106-114 (2012).
Wang, Y. et al., Systemic delivery of modified mRNA encoding herpes simplex virus 1 thymidine kinase for targeted camcer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Wetzer, B. et al., Reducible cationic lipids for gene transfer, Journal of Biochemistry, 356:745-756 (2001).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A Simple, Highly Efficient Method for Heterologous Expression in Mammalian Primary Neurons Using Cationic Lipid-mediated mRNA Transfection, Frontiers in Neuroscience, 4:181 (2010).
Wolf, J.A. et al., Protein/Amphipathic Polyamine Complexes Enable Highly Efficient Transfection with Minimal Toxicity, BioTechniques, 23:139-147 (1997).
Wu, J. and Zern, M., Modification of liposomes for liver targeting, Journal of Hepatology, 24(6):757-763 (1996).
Yamamoto et al., Important Role of the Proline Residue in the Signal Sequence that Directs the Secretion of Human Lysozyme in *Saccharomyces cerevisiae*, Biochemistry, 28:2728-2732 (1989).
Yamamoto, A. et al., Current prospects for mRNA gene delivery, European Journal of Pharmaceutics and Biopharmaceutics, 71:484-489 (2009).
Yasuda et al., Fabry Disease: Novel [alpha]-Galactosidase A 3-terminal Mutations Result in Multiple Transcripts Due to Aberrant 3-End Formation, American Journal of Human Genetics, 73: 162-73 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Zou, S. et al., Lipid-mediated delivery of RNA is more efficient than delivery of DNA in non-dividing cells, International Journal of Pharmaceutics, 389(1-2):232-243 (2010).
U.S. Appl. No. 61/494,714, filed Jun. 8, 2011.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Anderson, D.G. et al., Structure/property studies of polymeric gene delivery using a library of poly(beta-amino esters). Molecular Therapy 11(3):426-434 (2005).

(56) References Cited

OTHER PUBLICATIONS

Anderson, J. Biological Responses to Materials. Annual Review of Materials Research 31:81-110 (2001).
Anderson, W. French, Human gene therapy, Nature, 392, 25-30 (1998).
Author Unknown, Blood Proteins, published by WikiPedia, San Francisco, CA, 2 pages, <http://en.wikipedia.org/wiki/Biood_proteins> downloaded May 17, 2015.
Bahlke, M. A. et al., Progress towards in vivo use of siRNAs, Molecular Therapy, 13:644-670 (2006).
Bajaj, A. et al., Synthesis and gene transfection efficacies of PEI-cholesterol-based lipopolymers. Bioconjugate Chemistry 19(8): 1640-516511 (2008).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129(1972).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Burger, G. et al., Sequencing complete mitochondrial and plastid genomes, Nature Protocols, 2: 603-614 (2007).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Cotten, M. et al., Receptor-mediated transport of DNA into eukaryotic cells. Methods in Enzymology 217 (H):618-644 (1993).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235)404-410. Review (1995).
Damen, M. et al., Delivery of DNA and siRNA by novel gemini-like amphiphilic peptides. Journal of Controlled Release 145(1):33-39 (2010).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Decher, G. Fuzzy Nanoassemblies: Toward Layered Polymeric Multicomposites. Science 277: 1232-1237 (1997).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N"-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146(1999).
Discher, D.E. and Eisenberg, A., Polymer vesicles. Science 297(5583):967-973. Review (2002).
Driscoll, K.E. et al., Intratracheal instillation as an exposure technique for the evaluation of respiratory tract toxicity: uses and limitations, Toxicol. Sci., 55(1): 24-35 (2000).
Dwarki, V. et al.. Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fenske, D.B. and Cullis, P., Liposomal nanomedicines. Expert Opinion on Drug Delivery 5(1):25-44 (2008).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6): 1068-1074 (1999).
Grayson, A.C.R. et al., Biophysical and structural characterization of polyethylenimine-mediated siRNA delivery in vitro. Pharmaceutical Research 23(8): 1868-1876 (2006).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).

(56) References Cited

OTHER PUBLICATIONS

Haensler, J. and Szoka, F., Polyamidoamine cascade polymers mediate efficient transfection of cells in culture. Bioconjugate Chemistry 4(5):372-379 (1993).

Haskins M., Gene Therapy for Lysosomal Storage Disorders (LDSs) in Large Animal Models, ILAR J., 50(2):112-121 (2009).

Henkin, R. I. et al., Inhaled Insulin—Intrapulmonary, intranasal, and other routes of administration: Mechanisms of action, Nutrition, 26: 33-39 (2010).

Hill, I.R.C. et al., In vitro cytotoxicity of poly(amidoamine)s: relevance to DNA delivery. Biochimica et Biophysica Acta 1427: 161-174 (1999).

Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).

Hofland, H.E.J et al., Formation of stable cationic lipid/DNA complexes for gene transfer. Proceedings of the National Academy of Sciences of the USA 93 (14): 7305-7309 (1996).

*Homo sapiens* galactosidase, alpha (GLA) mRNA, NCBI Reference Sequence NM_000169.1, Modification Date: Nov. 17, 2006.

Hope, M.J. et al., Cationic Lipids, Phosphatidylethanolamine and the Intracellular Delivery of Polymeric, Nucleic Acid-Based Drugs. Molecular Membrane Technology 15:1-14 (1998).

Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).

Howard, K.A. Delivery of RNA interference therapeutics using polycation-based nanoparticles. Advanced Drug Delivery Reviews 61: 710-720 (2009).

Incani, V. et al., Lipid and hydrophobic modification of cationic carriers on route to superior gene vectors. Soft Matter 6: 2124-2138 (2010).

International Preliminary Report on Patentability for PCT/US2010/058457, 12 pages (dated Jun. 14, 2012).

Jiang, G. et al., Hyaluronic acid-polyethyleneimine conjugate for target specific intracellular delivery of siRNA. Biopolymers 89 (7): 635-642 (2008).

Jiang, M. et al., Electrochemically controlled release of lipid/DNA complexes: a new tool for synthetic gene delivery system. Electrochemistry Communications (6): 576-582 (2004).

Jiang, S. and Cao, Z., Ultralow-fouling, functionalizable, and hydrolyzable zwitterionic materials and their derivatives for biological applications. Advanced Materials 22(9):920-932 (2010).

Jolck, R.I. et al., Solid-phase synthesis of PEGylated lipopeptides using click chemistry. Bioconjugate Chemistry 21 (5):807-810 (2010).

Jon, S. et al., Degradable poly(amino alcohol esters) as potential DNA vectors with low cytotoxicity. Biomacromolecules 4(6): 1759-1762 (2003).

Kabanov, A.V. and Kabanov, V.A., DNA complexes with polycations for the delivery of genetic material into cells. Bioconjugate Chemistry 6(1): 7-20 (1995).

Kamath, S. et al., Surface chemistry influences implant-mediated host tissue responses. Journal of Biomedical Materials Research A 86(3):617-626 (2007).

Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).

Kaur, T. et al., Addressing the Challenge: Current and Future Directions in Ovarian Cancer THerapy, Current Gene THerapy, 9: 434-458 (2009).

Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).

Kim, T. et al., Synthesis of biodegradable cross-linked poly(beta-amino ester) for gene delivery and its modification, inducing enhanced transfection efficiency and stepwise degradation. Bioconjugate Chemistry 16(5): 1140-1148 (2005).

Kodama, K. et al., The Features and Shortcomings for Gene Delivery of Current Non-Viral Carriers, Current Medicinal Chemistry, 13: 2155-2161 (2006).

Lee, S. et al., Stability and cellular uptake of polymerized siRNA (poly-siRNA)/polyethylenimine (PEI) complexes for efficient gene silencing. Journal of Controlled Release 141: 339-346 (2010).

Lim, Y. et al., A self-destroying polycationic polymer: biodegradable poly(4-hydroxy-l-proline ester). Journal of American Chemical Society 121: 5633-5639 (1999).

Liu, Y. et al., Factors influencing the efficiency of cationic liposome-mediated intravenous gene delivery, Nature Biotechnology, 15:167-173 (1997).

Lorenzi, J. C. C. et al., Intranasal Vaccination with Messenger RNA as a New Approach in Gene Therapy: Use Against Tuberculosis, BMC Biotechnology, 10(77):1-11 (2010).

Lukyanov, A.N. and Torchilin, V.P., Micelles from lipid derivatives of water-soluble polymers as delivery systems for poorly soluble drugs. Advanced Drug Delivery Reviews 56: 1273-1289 (2004).

Luo, D. and Saltzman, M., Synthetic DNA delivery systems. Nature Biotechnology 18: 33-37. Review (2000).

Lynn, D.M. and Langer, R., Degradable Poly(ß-amino esters):? Synthesis, Characterization, and Self-Assembly with Plasmid DNA. Journal of American Chemical Society 122(44): 10761-10768 (2000).

Lynn, D.M. et al., Accelerated discovery of synthetic transfection vectors: parallel synthesis and screening of a degradable polymer library. Journal of American Chemical Society 123 (33): 8155-8156 (2001).

Lynn, D.M. et al., pH-Responsive Polymer Microspheres: Rapid Release of Encapsulated Material within the Range of Intracellular pH. Angewandte Chemie International Edition 40(9): 1707-1710 (2001).

Ma, M. et al., Development of Cationic Polymer Coatings to Regulate Foreign Body Responses. Advanced Healthcare Materials 23: H189-H194. Reviews (2011).

Margus, H. et al., Cell-penetrating peptides as versatile vehicles for oligonucleotide delivery. Molecular Therapy 20 (3): 525-533 (2012).

Martell, A.E. and Chaberek, S., The Preparation and the Properties of Some N,N'-Disubstituted-ethylenediaminedipropionic Acids. Journal of the American Chemical Society 72: 5357-5361 (1950).

Mathiowitz, E. and Langer, R., Polyanhydride microspheres as drug carriers I. Hot-melt microencapsulation. Journal of Controlled Release 5: 13-22 (1987).

Mathiowitz, E. et al., Novel microcapsules for delivery systems. Reactive Polymers 6: 275-283 (1987).

Mathiowitz, E. et al., Polyanhydride microspheres as drug carriers II. Microencapsulation by solvent removal. Journal of Applied Polymer Sciences 35: 755-774 (1988).

Mendelsohn, J.D. et al., Rational design of cytophilic and cytophobic polyelectrolyte multilayer thin films. Biomacromolecules 4(1): 96-106 (2003).

Miller, A. Cationic Liposomes for Gene Therapy. Angewandte Chemie International Edition 37: 1768-1785 (1998).

Narang, A.S. et al., Cationic lipids with increased DNA binding affinity for nonviral gene transfer in dividing and nondividing cells. Bioconjugate Chemistry 16(1): 156-168 (2005).

Navarro, G. et al., Phospholipid-polyethylenimine conjugate-based micelle-like nanoparticles for siRNA delivery. Drug Delivery and Translational Research 1:25-33 (2011).

Neamnark, A. et al., Aliphatic lipid substitution on 2 kDa polyethylenimine improves plasmid delivery and transgene expression. Molecular Pharmaceutics 6(6): 1798-1815 (2009).

Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).

Nguyen, D.N. et al., Drug delivery-mediated control of RNA immunostimulation. Molecular Therapy 17(9): 1555-1562 (2009).

Nori, A. et al., Tat-conjugated synthetic macromolecules facilitate cytoplasmic drug delivery to human ovarian carcinoma cells, Bioconj. Chem., 14(1): 44-50 (2003).

(56) References Cited

OTHER PUBLICATIONS

Ozer, A., Alternative applications for drug delivery: nasal and pulmonary routes, Nanomaterials and Nanosystems for Biomedical Applications, M.R. Mozafari (ed.): 99-112 (2007).
Painter, H., An Investigation of mRNA as a Gene Transfer Agent, Gene Medicine Research Group Nuffield Department of Clinical Laboratory Sciences and Merton College, University of Oxford, 1-282 (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).
Ratner, B.D. and Bryant, S., Biomaterials: where we have been and where we are going. Annual Review of Biomedical Engineering 6: 41-75 (2004).
Remington: The Science and Practice of Pharmacy, 21st Edition, Philadelphia, PA. Lippincott Williams & Wilkins (2005).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Siegwart, D.J. et al., Combinatorial synthesis of chemically diverse core-shell nanoparticles for intracellular delivery. Proceedings of the National Academy of the Sciences of the USA 108(32):12996-123001 (2011).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA to Degradable Lipid-Coated Polymeric Nanoparticles, Polymer Preprints, 51(2):668-669 (2010).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsvetkov, D.E. et al., Neoglycoconjugates based on dendrimeric poly(aminoamides). Russian Journal of Bioorganic Chemistry 28(6): 470-486 (2002).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Von Harpe et al., Characterization of commercially available and synthesized polyethylenimines for gene delivery. Journal of Controlled Release 69(2):309-322 (2000).
Walde, P. et al.. Preparation of Vesicles (Liposomes). Encyclopedia of Nanoscience and Nanotechnology. Nalwa, ed. American Scientific Publishers, Los Angeles 9:43-79 (2004).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di-and polyamines. Journal of Organic Chemistry 26(1):184-88. Russian (1990).

(56) References Cited

OTHER PUBLICATIONS

Zaugg, H.E. et al., 3-Carboxy-2,5-piperazinedione and Derivatives. Journal of American Chemical Society 78(11):2626-2631 (1956).
Zauner, W. et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7): 1448-1455 (2008).
T. Wajima, et al., "Prediction of Human Pharmacokinetic Profile in Animal Scale Up Based on Normalizing Time Course Profiles", Journal of Pharmaceutical Sciences, vol. 93, No. 7, Jul. 2004, p. 1890-1900.
J. Ra, et al., Safety of Intravenous Infusion of Human Adipose Tissue-Derived Mesenchymal Stem Cells in Animals and Humans, Stem Cells and Development, vol. 20, No. 8, 2011, p. 1297-1308.
Patton, J., Market Trends in Pulmonary Therapies, Trends and Opportunities, VI: 372-377 (2007).

\* cited by examiner

SEQUENCE LISTING

```
<160> NUMBER OF SEQ ID NOS: 15

<210> SEQ ID NO 1
<211> LENGTH: 1863
<212> TYPE: RNA
<213> ORGANISM: Homo sapiens

<400> SEQUENCE: 1
gccggcgcgc cccugggagg gugagccggc gccgggccca ggcccggacc uggugggagg      60 cgggggagg uggggacgag gccuggggag gcgggccccg cccaucugca gguggcugug     120
aacgcugagc ggcuccaggc gggggccggg cccggggcg gggucugugg cgcgcguccc     180 cgccacugu ccccggucac cggcccugcc cccgggcccu gugcuuauaa ccugggaugg     240
gcaccccugc caguccugcu cugccgccug ccaccgcugc ccgagcccga gugguucacu     300
gcacugugaa aacagauucc agacgccggg aacucacgcc uccaauccca gacgcuaugu     360
ccagcaaagg cuccgugguu cuggccuaca guggcggccu ggacaccucg ugcauccucg     420
uguggcugaa ggaacaaggc uaugacguca uugccuaucu ggccaacauu ggccagaagg     480
aagacuucga ggaagccagg aagaaggcac ugaagcuugg ggccaaaaag guguucauug     540
aggaugucag cagggaguuu guggaggagu ucaucuggcc ggccauccag uccagcgcac     600
uguaugagga ccgcuaccuc cugggcaccu cucuugccag gcccugcauc gcccgcaaac     660
aaguggaaau cgcccagcgg gaggggccca aguaugugu ccacggcgcc acaggaaagg     720
ggaacgauca gguccgguu gagcucagcu gcuacucacu ggcccccag auaaagguca     780 uugcucccug gaggaugccu gaauucuaca accgguucaa gggccgcaau gaccugaugg     840
aguacgcaaa gcaacacggg auucccaucc cggucacucc caagaacccg uggagcaugg     900
augagaaccu caugcacauc agcuacgagg cuggaaucuu ggagaacccc aagaaccaag     960
cgccuccagg ucucuacacg aagacccagg acccagccaa agccccaac accccugaca    1020 uucucgagau cgaguucaaa aaagggguc cugugaaggu gaccaacguc aaggauggca    1080 ccaccccacca gaccuccuug gagcucuuca guaccugaa cgaagucgcg ggcaagcaug    1140
gcguggggcc uauugacauc guggagaacc gcuucauugg aaugaaguc cgagguaucu    1200 acgagacccc agcaggcacc auccuuuacc augcucauu agacaucgag gccuucacca    1260
uggaccggga agucgcaaa aucaaacaag gccugggcuu gaaauuugcu gagcuggugu    1320
auaccgguuu cuggcacagc ccugagugug aauuuguccc ccacugcauc gccaagucc    1380 aggagcgagu ggaagggaaa gugcaggugu ccguccucaa gggccaggug uacauccucg    1440
```

```
gccgggaguc cccacugucu cucuacaaug aggagcuggu gagcaugaac gugcagggug    1500
auuaugagcc aacugaugcc accggguuca ucaacaucaa uucccucagg cugaaggaau    1560
aucaucgucu ccagagcaag gucacugcca aauagacccg uguacaauga ggagcugggg    1620
ccuccucaau uugcagaucc cccaaguaca ggcgcuaauu guugugauaa uuuguaauug    1680
ugacuuguuc uccccggcug gcagcguagu ggggcugcca ggcccagcu uguucccug      1740 gucccccuga agccugcaaa cguugucauc gaagggaagg gugggggca gcugcggugg     1800 ggagcuauaa aaaugacaau uaaaagagac acuagucuuu uauuucuaaa aaaaaaaaaa    1860
aaa                                                                  1863
```

<210> SEQ ID NO 2
<211> LENGTH: 412
<212> TYPE: PRT
<213> ORGANISM: Homo sapiens

<400> SEQUENCE: 2

```
Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45

Lys Lys Ala Leu Lys Leu Gly Ala Lys Lys Val Phe Ile Glu Asp Val
    50                  55                  60

Ser Arg Glu Phe Val Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285
```

```
Ile Leu Tyr His Ala His Leu Asp Ile Glu Ala Phe Thr Met Asp Arg
        290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
                340                 345                 350

Val Leu Lys Gly Gln Val Tyr Ile Leu Gly Arg Glu Ser Pro Leu Ser
            355                 360                 365

Leu Tyr Asn Glu Glu Leu Val Ser Met Asn Val Gln Gly Asp Tyr Glu
        370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410

<210> SEQ ID NO 3
<211> LENGTH: 1239
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
augagcagca agggcagcgu ggugcuggcc uacagcggcg gccuggacac cagcugcauc    60 cuggugugge ugaaggagca gggcuacgac gugaucgccu accuggccaa caucggccag   120
aaggaggacu ucgaggaggc cgcaagaaag gcccugaagc ugggcgccaa gaaggguuuc   180
aucgaggacg ugaccgcga guucguggag gaguucaucu ggcccgccau ccagagcagc   240
gcccuguacg aggaccgcua ccugcugggc accagccugg cccgccccug caucgcccgc   300
aagcaggugg agaucgccca gcgcgagggc gccaaguacg ugagccacgg cgccaccggc   360
aagggcaacg accaggugcg cuucgagcug agcugcuaca gccuggcccc ccagaucaag   420
gugaucgccc ccuggcgcau gcccgaguuc uacaaccgcu ucaagggccg caacgaccug   480
auggaguacg ccaagcagca cggcaucccc auccccguga cccccaagaa ccccuggagc   540
auggacgaga accugaugca caucagcuac gaggccggca uccuggagaa ccccaagaac   600 caggccccc ccggccugua caccaagacc caggaccccg ccaaggcccc caacaccccc   660
gacauccugg agaucgaguu caagaagggc gugcccguga aggugaccaa cgugaaggac   720
ggcaccaccc accagaccag ccuggagcug uucaauguac ugaacgaggu ggccggcaag   780
cacggcgugg ccgcaucga caucguggag aaccgcuuca ucggcaugaa gagccgcggc   840
aucuacgaga ccccgccgg caccauccug uaccacgccc accuggacau cgaggccuuc   900
accauggacc gcgaggugcg caagaucaag cagggccugg ccugaaguu cgccgagcug   960 guguacaccg gcuucuggca cagccccgag ugcgaguucg ugcgccacug caucgccaag  1020
agccaggagc gcguggaggg caaggugcag gugagcguac ugaagggcca ggugacauc  1080 cugggccgcg agagccccuu gagccuguac aacgaggagc uggugagcau gaacgugcag  1140
ggcgacuaca gcccaccga cgccaccggc uucaucaaca ucaacagccu gcgccugaag  1200
gaguaccacc gccugcagag caaggugacc gccaaguga                         1239
```

<210> SEQ ID NO 4
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggacagaucg ccuggagacg ccauccacgc uguuugacc uccauagaag acaccgggac      60
cgauccagcc uccgcggccg ggaacggugc auuggaacgc ggauuccccg ugccaagagu    120
gacucaccgu ccuugacacg                                                140

<210> SEQ ID NO 5
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
cggguggcau cccugugacc cucccagu gccucuccug gcccuggaag uugccacucc       60
agugcccacc agccuugucc uaauaaaauu aaguugcauc aagcu                    105

<210> SEQ ID NO 6
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
ggguggcauc ccugugaccc ucccccagug ccucuccugg cccuggaagu ugccacucca     60
gugcccacca gccuuguccu aauaaaauua aguugcauca aagcu                    105

<210> SEQ ID NO 7
<211> LENGTH: 1484
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
ggacagaucg ccuggagacg ccauccacgc uguuugacc uccauagaag acaccgggac      60
cgauccagcc uccgcggccg ggaacggugc auuggaacgc ggauuccccg ugccaagagu    120
gacucaccgu ccuugacacg augagcagca agggcagcgu ggugcuggcc uacagcggcg    180
gccuggacac cagcugcauc cuggugugg ugaaggagca gggcuacgac gugaucgccu     240
accuggccaa caucggccag aaggaggacu ucgaggaggc ccgcaagaag gcccugaagc    300
ugggcgccaa gaagguguuc aucgaggacg ugagccgcga guucguggag gaguucaucu    360
ggcccgccau ccagagcagc gcccuguacg aggaccgcua ccugcgggc ccagccugg     420 cccgccccug caucgcccgc aagcaggugg agaucgccca gcgcgagggc gccaaguacg    480
ugagccacgg cgccaccggc aagggcaacg accagguggc ccuucgagcug agcugcuaca    540 gccuggcccc ccagaucaag gugaucgccc ccuggcgcau gcccgaguuc uacaaccgcu    600

```
ucaagggccg caacgaccug auggaguacg ccaagcagca cggcaucccc auccccguga        660
cccccaagaa cccuggagc auggacgaga accugaugca caucagcuac gaggccggca         720
uccuggagaa cccaagaac caggcccccc ccggccugua caccaagacc caggaccccg         780
ccaaggcccc caacacccc gacauccugg agaucgaguu caagaagggc gugcccguga         840
aggugaccaa cgugaaggac ggcaccaccc accagaccag ccuggagcug uucauguacc        900
ugaacgaggu ggccggcaag cacggcgugg ccgcaucga caucguggag aaccgcuuca        960
ucggcaugaa gagccgcggc aucuacgaga ccccgccgg caccauccug uaccacgccc       1020
accuggacau cgaggccuuc accauggacc gcgaggugcg caagaucaag cagggccugg       1080
gccugaaguu cgccgagcug guguacaccg gcuucuggca cagccccgag ugcgaguucg       1140
ugcgccacug caucgccaag agccaggagc gcguggaggg caaggugcag gugagcgugc       1200
ugaagggcca ggugugacauc cugggccgcg agagccccu gagccuguac aacgaggagc       1260
uggugagcau gaacgugcag ggcgacuacg agcccaccga cgccaccggc uucaucaaca       1320
ucaacagccu gcgccugaag gaguaccacc gccugcagag caaggugacc gccaagugac       1380
ggguggcauc ccugugaccc cuccccagug ccucuccugg cccuggaagu gccacuccca       1440
gugcccacca gccuuguccu aauaaaauua aguugcauca agcu                        1484
```

<210> SEQ ID NO 8
<211> LENGTH: 1484
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8

```
ggacagaucg ccuggagacg ccauccacgc uguuuugacc uccauagaag acaccgggac         60
cgauccagcc uccgcggccg ggaacggugc auuggaacgc ggauucccg ugccaagagu        120 gacucaccgu ccuugacacg augagcagca agggcagcgu ggugcuggcc uacagcggcg        180
gccuggacac cagcugcauc cugguguggc ugaaggagca gggcuacgac gugaucgccu        240
accuggccaa caucggccag aaggaggacu ucgaggaggc cgcaagaag gcccugaagc        300 ugggcgccaa gaaggguuuc aucgaggacg ugagccgcga guucguggag gaguucaucu        360
ggcccgccau ccagagcagc gcccuguacg aggaccgcua ccugcugggc accagccugg       420
cccgccccug caucgcccgc aagcaggugg agaucgccca gcgcgagggc gccaaguacg       480
ugagccacgg cgccaccggc aagggcaacg accaggugcg cuucgagcug agcugcuaca       540
gccuggcccc ccagaucaag gugaucgccc ccugggcgcau gcccgaguuc acaaccgcu      600 ucaagggccg caacgaccug auggaguacg ccaagcagca cggcaucccc auccccguga       660
cccccaagaa cccuggagc auggacgaga accugaugca caucagcuac gaggccggca        720
uccuggagaa cccaagaac caggcccccc ccggccugua caccaagacc caggaccccg        780
ccaaggcccc caacacccc gacauccugg agaucgaguu caagaagggc gugcccguga        840
aggugaccaa cgugaaggac ggcaccaccc accagaccag ccuggagcug uucauguacc       900
ugaacgaggu ggccggcaag cacggcgugg ccgcaucga caucguggag aaccgcuuca       960
ucggcaugaa gagccgcggc aucuacgaga ccccgccgg caccauccug uaccacgccc       1020
accuggacau cgaggccuuc accauggacc gcgaggugcg caagaucaag cagggccugg      1080
gccugaaguu cgccgagcug guguacaccg gcuucuggca cagccccgag ugcgaguucg      1140
```

-continued

```
ugcgccacug caucgccaag agccaggagc gcguggaggg caaggugcag gugagcgugc    1200
ugaagggcca gguguacauc cugggccgcg agagccccu  gagccuguac aacgaggagc    1260
uggugagcau gaacgugcag ggcgacuacg agcccaccga cgccaccggc uucaucaaca    1320
ucaacagccu gcgccugaag gaguaccacc gccugcagag caaggugacc gccaagugag    1380 ggugcaucc  cugugacccc uccccaguqc cucuccuggc ccuggaaguu gccacuccag    1440 ugccccaccag ccuuguccua auaaaauuaa guugcaucaa agcu                    1484
```

<210> SEQ ID NO 9
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 10-300 nucleotides
<220> FEATURE:
<223> OTHER INFORMATION: See specification as filed for detailed
      description of substitutions and preferred embodiments

<400> SEQUENCE: 9

```
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
```

<210> SEQ ID NO 10
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10-200 nucleotides
<220> FEATURE:
<223> OTHER INFORMATION: See specification as filed for detailed
      description of substitutions and preferred embodiments

<400> SEQUENCE: 10

```
cccccccccc cccccccccc cccccccccc cccccccccc cccccccccc cccccccccc     60
cccccccccc cccccccccc cccccccccc cccccccccc cccccccccc cccccccccc    120
cccccccccc cccccccccc cccccccccc cccccccccc cccccccccc cccccccccc    180
cccccccccc cccccccccc                                                 200
```

<210> SEQ ID NO 11
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 10-500 nucleotides
<220> FEATURE:

<223> OTHER INFORMATION: See specification as filed for detailed
      description of substitutions and preferred embodiments

<400> SEQUENCE: 11
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa                                                 500

<210> SEQ ID NO 12
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

<400> SEQUENCE: 12
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa                                                            250

<210> SEQ ID NO 13
<211> LENGTH: 1239
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
augagcucaa agggaucugu ggugcuggca uacucggggg gauuggacac uucaugcaua      60
cuugucuggu ugaaggaaca gggcuacgac gugaucgccu accugcuaa caucggucaa     120 aaggaggacu ucgaggaggc ccggaagaag gcccugaagc ugggcgcgaa gaaaguguuc     180
aucgaggacg ugucccggga auuuguggaa gaguucaucu ggcccgccau ccaaagcagc     240
gcacuguacg aggauagaua ccuccucgga acaucccuug cccggccaug uauugccagg     300
aaacaggugg aaaucgccca gcgggaagga gccaaauacg ugucccacgg ggcgaccgga     360
aaggggaacg accaagugcg cuucgagcug ucgugcuacu cccuggcacc gcagauuaag     420
gucaucgcgc cguggagaau gccugaauuc uacaaccgcu ucaagggccg caacgaucug     480
auggaauacg ccaagcagca cggcaucccg auccccguga ccccuaagaa cccuugguca     540
auggacgaga aucugaugca caucagcuac gaagcgggca uccuggagaa ccccaagaau     600
caagcuccgc ccggacugua cacuaagacu caggaucccg cuaaggcgcc caacacuccu     660

| | |
|---|---|
| gauauuuugg aaaucgaauu caagaagggu gucccaguga aggucaccaa cgugaaggac | 720 |
| ggcacuaccc accagaccuc gcuggaacug uuuauguauc ugaacgaggu ggccggcaaa | 780 |
| cauggagucg gcagaaucga uauuguggag aaccgcuuua uuggcaugaa guccaggggg | 840 |
| aucuaugaaa ccccggccgg aaccauccuc uaccacgccc aucucgacau ugaagcguuc | 900 |
| accauggacc gcgaggyccg caagauuaag cagggccugg acucaaguu cgccgagcuc | 960 |
| guguacaccg guucuggca uccccggaa ugcgaauucg ugcgacacug cauugccaag | 1020 |
| agccaggagc ggguggaagg aaaggyccag gugyccgygc ugaaggyuca aguyacauc | 1080 |
| cuggggcggg aguccccucu uccccuguac aacgaagaac ugguygyugau gaacgygcag | 1140 |
| ggagacuacg agccgaccga cgccacgggy uucauuaaca ucaauuccccu gagacugaag | 1200 |
| gaguaccacc ggcuccaguc caaagucacc gcuaaguga | 1239 |

<210> SEQ ID NO 14
<211> LENGTH: 1239
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 14

| | |
|---|---|
| augagcucaa aaggaucggu ggugcuggca uacucgggag gauuggacac uucauguauu | 60 |
| cuugucuggc ucaaggaaca gggcuacgac gucauugccu accuggccaa caucggucag | 120 |
| aaagaggacu ucgaggaagc cagaaagaag gcccugaagc uggagccaa gaaggyguuc | 180 |
| aucgaggacg ugucccgcga auuguggaa gaauucaucu ggccugccau ucaauccucc | 240 |
| gcgcucuacg aggaucggua ccuucuggga acuuccuugg cucgcccgug caucgcccgg | 300 |
| aaacaagugg agauugcaca gcgggaagga gcuaaguacg uguccacgg ggccacugga | 360 |
| aagggcaacg aucaagugcg cuucgagcug uccugcuacu cccuggcgcc acagaucaag | 420 |
| gucaucgcgc cguggcggau gcccgaguuc uauaaccgcu ucaagggacg gaacgaucug | 480 |
| auggaguacc ccaagcagca cggcauuccg auacccguga cccccaagaa cccuuggagc | 540 |
| auggacgaga accugaugca uaucucuuac gaagccggga uucucgaaaa cccuaagaau | 600 |
| caggcgccgc cuggccugua caccaaaacc caggaccccg ccaaggcgcc gaacacgccc | 660 |
| gacauccucg aaaucgaguu caagaagggg gugccaguga aggucaccaa cgugaaggac | 720 |
| ggaaccaccc aucagaccuc acuggaacuc uucauguacc ucaacgaggu cgcagggaag | 780 |
| cacggcgugg ggagaaucga caucguggaa aacagguuca ucggcaugaa gucccgggga | 840 |
| aucuacgaaa cacccgccgg gacuauccuc uaccacgccc accuggacau ugaggccuuc | 900 |
| accauggaua gagaagugcg caagauuaag cagggucugg gucugaaguu cgccgaguug | 960 |
| gucuacaccg gauucuggca uccccugaaa ugcgaauucg ugcgccacug cauugccaag | 1020 |
| agccaggaaa gaguggaggg caaagccaag gucgcgygc ugaagggcca aguyacauc | 1080 |
| cuggggaggg aaagcccgcu cucccuguac aacgaggaac ugguygyugau gaacgyccag | 1140 |
| ggcgauyaug agccgacuga cgccacyggu uuuaucaaua ucaacagccu gcgacugaag | 1200 |
| gaguaccacc ggcugcaguc caaggycacc gcuaaguag | 1239 |

<210> SEQ ID NO 15
<211> LENGTH: 1239
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 15

```
augagcucga aaggauccgu gguuuuggca uacuccggug gacuugacac uucaugcauu    60
uugguuuggc ucaaagaaca gggcuacgau gugaucgccu accuggcgaa caucggacag   120
aaagaggacu uugaagaggc ccgcaagaag gcacugaagc ugggugccaa gaaaguguuu   180
aucgaggaug ugucgagaga auucguggaa gaauucauuu ggccagccau ucaaagcucc   240
gcgcuguacg aggacagaua ccuccucggc accucacugg cccgcccuug caucgcgcgc   300
aaacaggucg agaucgcuca aagagaagga gcuaaauacg ugcacacgg cgccaccgga    360
aagggaaaug accaagccg cuucgagcug ucuugcuacu cacucgcucc gcaaaucaag    420
gucaucgcac cguggaggau gcccgaguuc uacaaccggu ucaaggggcg gaacgaccug   480
auggaguacg cgaagcagca cgguaucccg auccuguca ccccaaagaa ccccuggagc    540
auggacgaaa aucugaugca caucagcuac gaagcaggaa uccuggagaa cccgaaaaau   600
caagcaccuc cuggacugua cacuaagacc caggacccag ccaaggcccc gaauaccccg   660
gacaucuugg aaaucgaguu caagaagggg gugccagug aagguuaccaa ugucaaggau    720
gggaccacuc accaaacuag ccuggaacug uucauguacc ugaacgaagu ggcuggaaaa   780
cauggcgugg gaagaaucga uaucguggag aaccgcuuca ucggcaugaa gucaagggga   840
aucuacgaaa cuccggccgg gacgauacug uaucaugcgc aucucgacau ugaagccuuu   900
acuauggauc gggaaguccg aaagaucaaa cagggcuugg gccucaaguu ugccgagcug   960
guguacacgg gauucuggca cucgccggaa ugcgaauucg ugcgccacug uauugcgaag  1020
ucccaggagc gcguggaagg gaagguccaa gucuccgugc ucaaaggaca ggucuacauc  1080
cuuggacggg agucgcccu gucgcucuac aacgaagaac uggugucgau gaacgugcag   1140
ggagacuaug aaccaacgga ugcuacuggu uucaucaaca ucaauucgcu gcggcuuaag   1200
gaguaccauc ggcugcaguc caaggucacc gcgaaguag                          1239
```

MRNA THERAPY FOR ARGININOSUCCINATE SYNTHETASE DEFICIENCY

RELATED APPLICATIONS

This application claims priority to U.S. Provisional Application Ser. No. 61/894,294, filed Oct. 22, 2013, the disclosure of which is hereby incorporated by reference.

The instant application contains a Sequence Listing which has been submitted electronically in ASCII format and is hereby incorporated by reference in its entirety. Said ASCII copy, created on Dec. 22, 2014, is named "2006685-0691_SL.txt" and is 22,079 bytes in size. The entire contents of the Sequence Listing are herein incorporated by reference.

BACKGROUND

Argininosuccinate Synthetase Deficiency (ASD) is an autosomal recessive metabolic genetic disorder characterized by a mutation in the gene for the enzyme argininosuccinate synthetase (ASS1), affecting its ability to bind to citrulline, aspartate and other molecules. Defects in the ASS protein disrupt the urea cycle and prevent the liver from properly processing excess nitrogen into urea. An accumulation of ammonia and other byproducts of the urea cycle (such as citrulline) is toxic and when it occurs during the first few days of life can lead to symptoms such as lack of energy (lethargy) poor feeding, vomiting, seizures and loss of consciousness. Currently, there is no cure for the disease and standard of care is through management of diet, minimizing foods that contain high amounts of protein, and dietary supplements of arginine and phenylacetate.

SUMMARY OF THE INVENTION

The present invention provides, among other things, improved methods and compositions for the treatment of Argininosuccinate Synthetase Deficiency (ASD) based on mRNA therapy. The invention encompasses the observation that administration of an mRNA encoding a human ASS1 protein, encapsulated within a liposome, resulted in highly efficient and sustained protein production in vivo and successful reduction of plasma ammonia levels, a clinically-relevant disease marker.

In one aspect, the present invention provides a method of treating ASD, including administering to a subject in need of treatment a composition comprising an mRNA encoding argininosuccinate synthetase (ASS1) at an effective dose and an administration interval such that at least one symptom or feature of ASD is reduced in intensity, severity, or frequency or has delayed in onset. In some embodiments, the mRNA is encapsulated within a liposome.

In another aspect, the present invention provides compositions for treating ASD comprising an mRNA encoding ASS1 at an effective dose amount encapsulated within a liposome.

In some embodiments, a suitable liposome comprises one or more cationic lipids, one or more non-cationic lipids, one or more cholesterol-based lipids and one or more PEG-modified lipids.

In some embodiments, the one or more cationic lipids are selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

In some embodiments, the one or more cationic lipids comprise a compound of formula I-c1-a:

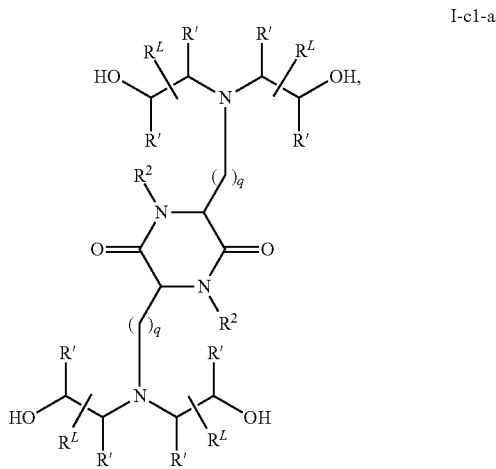

I-c1-a or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl; and each $R^L$ independently is $C_{8-12}$ alkyl.

In some embodiments, the one or more cationic lipids comprise cKK-E12:

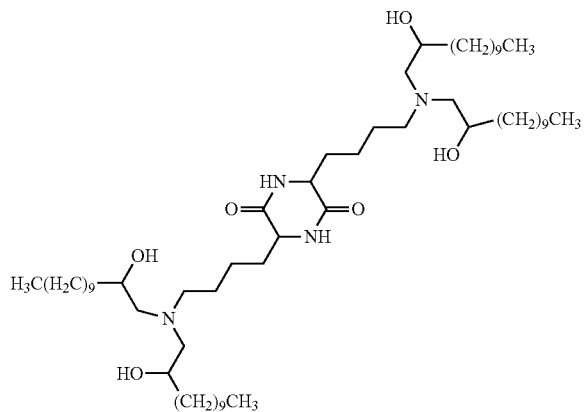

In some embodiments, the one or more non-cationic lipids suitable for the invention are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), and combinations thereof.

In some embodiments, the one or more cholesterol-based lipids are selected from cholesterol, PEGylated cholesterol and DC-Chol (N,N-dimethyl-N-ethylcarboxamidocholesterol), 1,4-bis(3-N-oleylamino-propyl)piperazine.

In some embodiments, the liposome further comprises one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K.

In some embodiments, a suitable liposome comprises a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In some embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, cationic lipids (e.g., cKK-E12, C12-200, ICE, and/or HGT4003) constitute about 30%, about 35%, about 40%, about 45%, about 50%, about 55%, or about 60% of the liposome by molar ratio.

In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) may be between about 30-60:25-35:20-30:1-15, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:30:20:10, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:30:25:5, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 40:32:25:3, respectively. In some embodiments, the ratio of cationic lipid(s) (e.g., cKK-E12, C12-200, ICE, and/or HGT4003) to non-cationic lipid(s) (e.g., DOPE) to cholesterol-based lipid(s) (e.g., cholesterol) to PEGylated lipid(s) (e.g., DMG-PEG2K) is approximately 50:25:20:5.

In some embodiments, the size of a liposome is determined by the length of the largest diameter of the liposome particle. In some embodiments, a suitable liposome has a size less than about 500 nm, 400 nm, 300 nm, 250 nm, 200 nm, 150 nm, 100 nm, 75 nm, or 50 nm. In some embodiments, a suitable liposome has a size less than about 100 nm, 90 nm, 80 nm, 70 nm, or 60 nm.

In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, the mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

In some embodiments, provided composition is administered intravenously. In some embodiments, provided composition is administered via pulmonary delivery. In certain embodiments, pulmonary delivery is performed by aerosolization, inhalation, nebulization or instillation. In some embodiments, provided compositions are formulated as respirable particles, nebulizable lipid, or inhalable dry powder.

In some embodiments, provided compositions are administered once daily, once a week, twice a month, once a month. In some embodiments, provided compositions are administered once every 7 days, once every 10 days, once every 14 days, once every 28 days or once every 30 days.

In some embodiments, the ASS1 protein is expressed in liver. In some embodiments, administering the provided composition results in the expression of an ASS1 protein level at or above about 100 ng/mg (e.g., at or above about 200 ng/mg, 400 ng/mg, 500 ng/mg, 1000 ng/mg, 2000 ng/mg or 3000 ng/mg) of total protein in the liver.

In some embodiments, administering of the composition results in increased serum ASS1 protein level. In some embodiments, administering of the composition results in increased serum ASS1 protein level by at least about 10%, 20%, 30%, 40%, 50%, 60%, 70%, 80%, 90%, 1-fold, 2-fold, 3-fold, 4-fold or 5-fold as compared to the baseline serum ASS1 protein level before the treatment.

In some embodiments, administering of the composition results in reduced citrulline level in the subject as compared to the baseline citrulline level before the treatment. In some embodiments, administering of the composition results in reduced plasma citrulline level by at least about 10%, 20%, 30%, 40%, 50%, 60%, 70%, 80%, 90%, or 95% as compared to the baseline plasma citrulline level before the treatment. In some embodiments, administering of the composition results in reduced plasma citrulline level to less than about 2000 µM, 1500 µM, 1000 µM, 750 µM, 500 µM, 250 µM, 100 µM, 90 µM, 80 µM, 70 µM, 60 µM, 50 µM, 40 µM, or 30 µM.

In some embodiments, administering of the composition results in reduced ammonia level in the subject as compared to the baseline ammonia level before the treatment. In some embodiments, administering the provided composition results in reduction of ammonia levels to about 3000 µmol/L or less, about 2750 µmol/L or less, about 2500 µmol/L or less, about 2250 µmol/L or less, about 2000 µmol/L or less, about 1750 µmol/L or less, about 1500 µmol/L or less, about 1250 µmol/L or less, about 1000 µmol/L or less, about 750 µmol/L or less, about 500 µmol/L or less, about 250 µmol/L or less, about 100 µmol/L or less, or about 50 µmol/L or less in the plasma or serum. In a particular embodiment, administering the provided composition results in reduction of ammonia levels to about 50 µmol/L or less in plasma or serum.

In some embodiments, administering the provided composition results in reduced ammonia level in a biological sample by at least about 10%, at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, or at least about 95% as compared to baseline ammonia level before treatment. Suitable biological sample may be whole blood, serum, plasma, or urine.

In some embodiments, the mRNA is codon optimized. In some embodiments, the codon-optimized mRNA comprises SEQ ID NO:3, SEQ ID NO:13, SEQ ID NO: 14 or SEQ ID NO:15 (corresponding to codon-optimized human ASS1 mRNA sequences). In some embodiments, the mRNA comprises the 5' UTR sequence of SEQ ID NO:4 (corresponding to 5' UTR sequence X). In some embodiments, the mRNA comprises the 3' UTR sequence of SEQ ID NO:5 (corresponding to a 3' UTR sequence Y). In some embodiments, the mRNA comprises the 3' UTR sequence of SEQ ID NO:6 (corresponding to a 3' UTR sequence Y). In some embodiments, the codon-optimized mRNA comprises SEQ ID NO:7 or SEQ ID NO:8 (corresponding to codon-optimized human ASS1 mRNA sequence with 5' UTR and 3' UTR sequences).

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methyl-cytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine. In some embodiments, the mRNA is unmodified.

In particular embodiments, the present invention provides a composition for treating ASD comprising an mRNA encoding argininosuccinate synthetase (ASS1) at an effective dose amount encapsulated within a liposome, wherein the mRNA comprises SEQ ID NO:3, SEQ ID NO:13, SEQ ID NO:14 or SEQ ID NO:15, and further wherein the liposome comprises cationic or non-cationic lipid, cholesterol-based lipid and PEG-modified lipid.

In particular embodiments, the present invention provides a composition for treating ASD comprising an mRNA encoding argininosuccinate synthetase (ASS1) at an effective dose amount encapsulated within a liposome, wherein the mRNA comprises SEQ ID NO:7 or SEQ ID NO:8, and further wherein the liposome comprises cationic or non-cationic lipid, cholesterol-based lipid and PEG-modified lipid.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
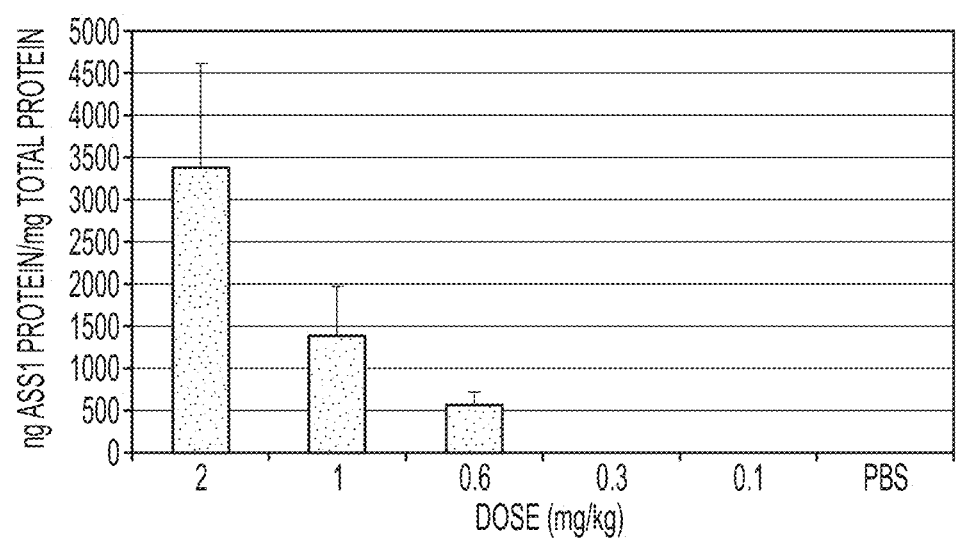
FIG. 1 depicts exemplary ASS1 protein levels detected via ELISA after treatment with human ASS1 mRNA-loaded cKK-E12-based lipid nanoparticles at various doses.
Figure 2A:
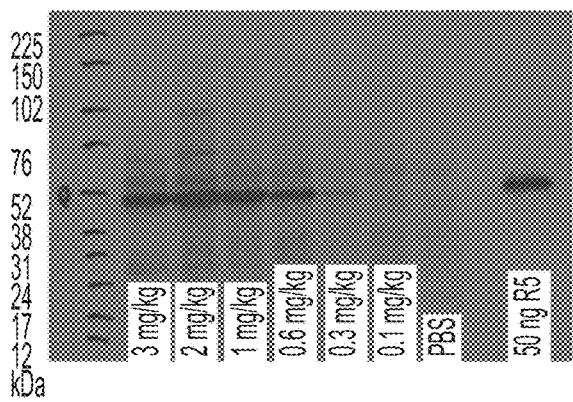
FIGS. 2A-2D depict exemplary Western blots comparing human ASS1 protein levels in liver as a function of dose after a single intravenous dose of human ASS1 mRNA-encapsulated lipid nanoparticles. CD 1 mice were sacrificed at 24 hours post-administration and livers were harvested and analyzed as described above. Human ASS1 protein was detected using 2H8 mouse monoclonal antibody. 50 micrograms total liver protein was loaded into each well. Recombinant human ASS1 protein was loaded on each gel as a positive control (R5 control).
Figure 2B:
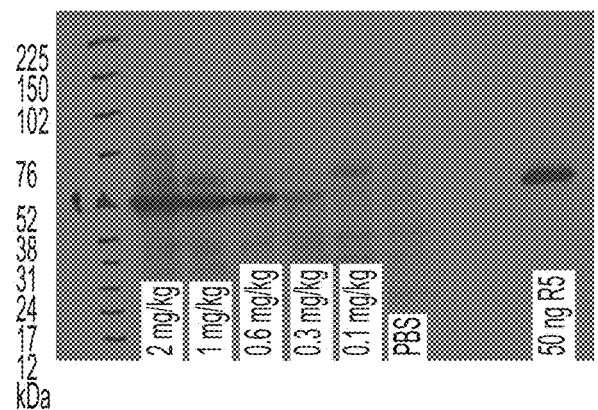
Figure 2C:
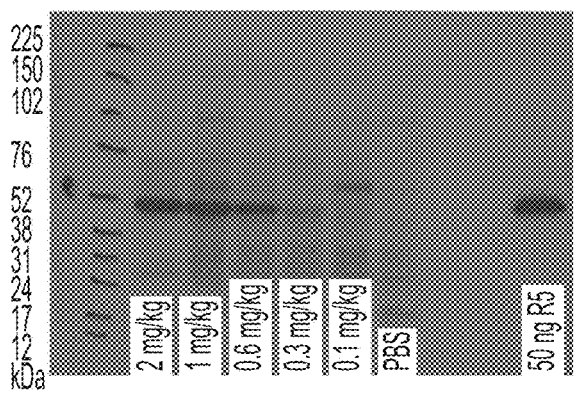
Figure 2D:
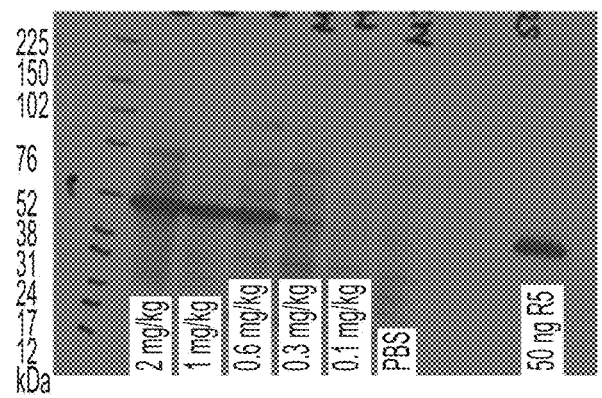

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for treating Argininosuccinate Synthetase Deficiency (ASD) based on mRNA therapy. In particular, the present invention provides methods for treating ASD by administering to a subject in need of treatment a composition comprising an mRNA encoding argininosuccinate synthetase (ASS) at an effective dose and an administration interval such that at least one symptom or feature of ASD is reduced in intensity, severity, or frequency or has delayed in onset. In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In some embodiments, a liposome suitable for the present invention contains cationic or non-cationic lipid(s), cholesterol-based lipid(s) and PEG-modified lipid(s).

Argininosuccinate Synthetase Deficiency (ASD)

The present invention may be used to treat a subject who is suffering from or susceptible to Argininosuccinate synthetase deficiency (ASD). ASD is an autosomal recessive metabolic genetic disorder characterized by a mutation in the gene for the enzyme argininosuccinate synthetase (ASS1). At least 50 mutations that cause type I ASD have been identified in the ASS1 gene. Most of these mutations involve single amino acid substitutions. Many of the mutations in the ASS1 gene likely affect the structure of the resulting protein and its ability to bind to citrulline, aspartate and other molecules. A few of the mutations in the ASS1 gene lead to the productions of an abnormally short version of the enzyme that cannot effectively play its role in the urea cycle.

Defects in the ASS1 protein disrupt the urea cycle and prevent the liver from properly processing excess nitrogen, which is generated when protein is used for energy, into urea. An accumulation of ammonia and other byproducts of the urea cycle (such as citrulline) is toxic and when it occurs during the first few days of life can lead to symptoms such as lack of energy (lethargy) poor feeding, vomiting, seizures and loss of consciousness. These medical problems can be life-threatening in many cases.

Compositions and methods described herein may be used to treat at least one symptom or feature of ASD.

Argininosuccinate Synthetase (ASS1)

In some embodiments, the present invention provides methods and compositions for delivering mRNA encoding ASS1 to a subject for the treatment of argininosuccinate synthetase deficiency (ASD). A suitable ASS1 mRNA encodes any full length, fragment or portion of an ASS1 protein which can be substituted for naturally-occurring ASS1 protein activity and/or reduce the intensity, severity, and/or frequency of one or more symptoms associated with ASD.

In some embodiments, a suitable mRNA sequence is an mRNA sequence encoding human ASS1 protein. The naturally-occurring human ASS1 mRNA sequence and the corresponding amino acid sequence are shown in Table 1:

TABLE 1

| Human ASS1 | |
|---|---|
| Human ASS1 (mRNA) | GCCGGCGCGCCCCUGGGAGGGUGAGCCGGCGCCGGGCCCAGGCCCGGACCUG<br>GUGGGAGGCGGGGGGAGGUGGGGACGAGGCCUGGGGAGGCGGGCCCCGCCC<br>AUCUGCAGGUGGCUGUGAACGCUGAGCGGCUCCAGGCGGGGCCGGGCCCGG<br>GGGCGGGGUCUGUGGCGCGCGUCCCCGCCACGUGUCCCCGGUCACCGGCCCU<br>GCCCCCGGGCCCUGUGCUUAUAACCUGGGAUGGGCACCCCUGCCAGUCCUGC<br>UCUGCCGCCUGCCACCGCUGCCCGAGCCCGAGUGGUUCACUGCACUGUGAAA<br>ACAGAUUCCAGACGCCGGGAACUCACGCCUCCAAUCCCAGACGCUAUGUCCA<br>GCAAAGGCUCCGUGGUUCUGGCCUACAGUGGCGGCCUGGACACCUCGUGCAU<br>CCUCGUGUGGCUGAAGGAACAAGGCUAUGACGUCAUUGCCUAUCUGGCCAA<br>CAUUGGCCAGAAGGAAGACUUCGAGGAAGCCAGGAAGAAGGCACUGAAGCU<br>UGGGGCCAAAAAGGUGUUCAUUGAGGAUGUCAGCAGGGAGUUUGUGGAGGA<br>GUUCAUCUGGCCGGCCAUCCAGUCCAGCGCACUGUAUGAGGACCGCUACCUC<br>CUGGGCACCUCUCUUGCCAGGCCCUGCAUCGCCCGCAAACAAGUGGAAAUCG<br>CCCAGCGGGAGGGGGCCAAGUAUGUGUCCCACGGCGCCACAGGAAAGGGGA<br>ACGAUCAGGUCCGGUUUGAGCUCAGCUGCUACUCACUGGCCCCCCAGAUAAA<br>GGUCAUUGCUCCCUGGAGGAUGCCUGAAUUCUACAACCGGUUCAAGGGCCGC<br>AAUGACCUGAUGGAGUACGCAAAGCAACACGGGAUUCCCAUCCCGGUCACUC<br>CCAAGAACCCGUGGAGCAUGGAUGAGAACCUCAUGCACAUCAGCUACGAGGC<br>UGGGAAUCCUGGAGAACCCCAAGAACCAAGCGCCUCCAGGUCUCUACACGAAG<br>ACCCAGGACCCAGCCAAAGCCCCCAACACCCCUGACAUUCUCGAGAUCGAGU<br>UCAAAAAAGGGGUCCCUGUGAAGGUGACCAACGUCAAGGAUGGCACCACCC<br>ACCAGACCUCCUUGGAGCUCUUCAUGUACCUGAACGAAGUCGCGGGCAAGCA<br>UGGCGUGGGCCGUAUUGACAUCGUGGAGAACCGCUUCAUUGGAAUGAAGUC<br>CCGAGGUAUCUACGAGACCCCAGCAGGCACCAUCCUUUACCAUGCUCAUUUA<br>GACAUCGAGGCCUUCACCAUGGACCGGGAAGUGCGCAAAAUCAAACAAGGCC<br>UGGGCUUGAAAUUUGCUGAGCUGGUGUAUACCGGUUUCUGGCACAGCCCUG |

TABLE 1-continued

Human ASS1

| | |
|---|---|
| | AGUGUGAAUUUGUCCGCCACUGCAUCGCCAAGUCCCAGGAGCGAGUGGAAG<br>GGAAAGUGCAGGUGUCCGUCCUCAAGGGCCAGGUGUACAUCCUCGGCCGGG<br>AGUCCCCACUGUCUCUCUACAAUGAGGAGCUGGUGAGCAUGAACGUGCAGG<br>GUGAUUAUGAGCCAACUGAUGCCACCGGGUUCAUCAACAUCAAUUCCCUCAG<br>GCUGAAGGAAUAUCAUCGUCUCCAGAGCAAGGUCACUGCCAAAUAGACCCG<br>UGUACAAUGAGGAGCUGGGGCCUCCUCAAUUUGCAGAUCCCCCAAGUACAG<br>GCGCUAAUUGUUGUGAUAAUUUGUAAUUGUGACUUGUUCUCCCCGGCUGGC<br>AGCGUAGUGGGGCUGCCAGGCCCCAGCUUUGUUCCCUGGUCCCCCUGAAGCC<br>UGCAAACGUUGUCAUCGAAGGGAAGGGUGGGGGGCAGCUGCGGUGGGGAGC<br>UAUAAAAAUGACAAUUAAAAGAGACACUAGUCUUUUAUUUCUAAAAAAAAA<br>AAAAAAA(SEQ ID NO: 1) |
| Human<br>ASS1<br>(Amino<br>Acid Seq.) | MSSKGSVVLAYSGGLDTSCILVWLKEQGYDVIAYLANIGQKEDFEEARKKALKLG<br>AKKVFIEDVSREFVEEFIWPAIQSSALYEDRYLLGTSLARPCIARKQVEIAQREGAK<br>YVSHGATGKGNDQVRFELSCYSLAPQIKVIAPWRMPEFYNRFKGRNDLMEYAKQ<br>HGIPIPVTPKNPWSMDENLMHISYEAGILENPKNQAPPGLYTKTQDPAKAPNTPDIL<br>EIEFKKGVPVKVTNVKDGTTHQTSLELFMYLNEVAGKHGVGRIDIVENRFIGMKSR<br>GIYETPAGTILYHAHLDIEAFTMDREVRKIKQGLGLKFAELVYTGFWHSPECEFVR<br>HCIAKSQERVEGKVQVSVLKGQVYILGRESPLSLYNEELVSMNVQGDYEPTDATG<br>FININSLRLKEYHRLQSKVTAK (SEQ ID NO: 2) |

In some embodiments, a suitable mRNA is a wild-type hASS1 mRNA of sequence (SEQ ID NO:1). In some embodiments, a suitable mRNA may be a codon optimized hASS1 sequence, such as the sequence shown below:

(SEQ ID NO: 3)
AUGAGCAGCAAGGGCAGCGUGGUGCUGGCCUACAGCGGCGGCCUGGACAC

CAGCUGCAUCCUGGUGUGGCUGAAGGAGCAGGGCUACGACGUGAUCGCCU

ACCUGGCCAACAUCGGCCAGAAGGAGGACUUCGAGGAGGCCCGCAAGAAG

GCCCUGAAGCUGGGCGCCAAGAAGGUGUUCAUCGAGGACGUGAGCCGCGA

GUUCGUGGAGGAGUUCAUCUGGCCCGCCAUCCAGAGCAGCGCCCUGUACG

AGGACCGCUACCUGCUGGGCACCAGCCUGGCCCGCCCCUGCAUCGCCCGC

AAGCAGGUGGAGAUCGCCCAGCGCGAGGGCGCCAAGUACGUGAGCCACGG

CGCCACCGGCAAGGGCAACGACCAGGUGCGCUUCGAGCUGAGCUGCUACA

GCCUGGCCCCCAGAUCAAGGUGAUCGCCCCCUGGCGCAUGCCCGAGUUC

UACAACCGCUUCAAGGGCCGCAACGACCUGAUGGAGUACGCCAAGCAGCA

CGGCAUCCCCAUCCCCGUGACCCCCAAGAACCCCUGGAGCAUGGACGAGA

ACCUGAUGCACAUCAGCUACGAGGCCGGCAUCCUGGAGAACCCCAAGAAC

CAGGCCCCCCCGGCCUGUACACCAAGACCCAGGACCCCGCCAAGGCCCC

CAACACCCCCGACAUCCUGGAGAUCGAGUUCAAGAAGGGCGUGCCCGUGA

AGGUGACCAACGUGAAGGACGGCACCACCCACCAGACCAGCCUGGAGCUG

UUCAUGUACCUGAACGAGGUGGCCGGCAAGCACGGCGUGGGCCGCAUCGA

CAUCGUGGAGAACCGCUUCAUCGGCAUGAAGAGCCGCGGCAUCUACGAGA

CCCCCGCCGGCACCAUCCUGUACCACGCCCACCUGGACAUCGAGGCCUUC

ACCAUGGACCGCGAGGUGCGCAAGAUCAAGCAGGGCCUGGGCCUGAAGUU

CGCCGAGCUGGUGUACACCGGCUUCUGGCACAGCCCCGAGUGCGAGUUCG

UGCGCCACUGCAUCGCCAAGAGCCAGGAGCGCGUGGAGGGCAAGGUGCAG

GUGAGCGUGCUGAAGGGCCAGGUGUACAUCCUGGGCCGCGAGAGCCCCCU

GAGCCUGUACAACGAGGAGCUGGUGAGCAUGAACGUGCAGGGCGACUACG

-continued
AGCCCACCGACGCCACCGGCUUCAUCAACAUCAACAGCCUGCGCCUGAAG

GAGUACCACCGCCUGCAGAGCAAGGUGACCGCCAAGUGA

Additional exemplary mRNA sequences are described in the Examples section below, for example, SEQ ID NO:7 and SEQ ID NO:8, both of which include 5' and 3' untranslated regions framing a coden-optimized ASS1-encoding mRNA.

In some embodiments, a suitable mRNA sequence may be an mRNA sequence a homolog or an analog of human ASS1 protein. For example, a homologue or an analogue of human ASS1 protein may be a modified human ASS1 protein containing one or more amino acid substitutions, deletions, and/or insertions as compared to a wild-type or naturally-occurring human ASS1 protein while retaining substantial ASS1 protein activity. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, an mRNA suitable for the present invention encodes a protein substantially identical to human ASS1 protein. In some embodiments, an mRNA suitable for the present invention encodes an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, an mRNA suitable for the present invention encodes a fragment or a portion of human ASS1 protein. In some embodiments, an mRNA suitable for the present invention encodes a fragment or a portion of human ASS1 protein, wherein the fragment or portion of the protein still maintains ASS1 activity similar to that of the wild-type protein. In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1, SEQ ID NO:3, SEQ ID NO:7, SEQ ID NO:8, SEQ ID NO:13, SEQ ID NO:14 or SEQ ID NO:15.

In some embodiments, a suitable mRNA encodes a fusion protein comprising a full length, fragment or portion of an ASS1 protein fused to another protein (e.g., an N or C terminal fusion). In some embodiments, the protein fused to the mRNA encoding a full length, fragment or portion of an ASS1 protein encodes a signal or a cellular targeting sequence.

Delivery Vehicles

According to the present invention, mRNA encoding an ASS1 protein (e.g., a full length, fragment or portion of an ASS1 protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding an ASS1 protein may be delivered via a single delivery vehicle. In some embodiments, mRNAs encoding an ASS1 protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z,12Z)-octadeca-9,12-dien-1-yl) tetracosa-15,18-dien-1-amine (HGT5000), (15Z,18Z)—N, N-dimethyl-6-((9Z,12Z)-octadeca-9,12-dien-1-yl)tetracosa-4,15,18-trien-1-amine (HGT5001), and (15Z,18Z)—N,N-dimethyl-6-((9Z,12Z)-octadeca-9,12-dien-1-yl)tetracosa-5,15,18-trien-1-amine (HGT5002).

In some embodiments, provided liposomes include a cationic lipid described in WO 2013063468 and in U.S. provisional application entitled "Lipid Formulations for Delivery of Messernger RNA" filed concurrently with the present application on even date, both of which are incorporated by reference herein.

In some embodiments, a cationic lipid comprises a compound of formula I-c1-a:

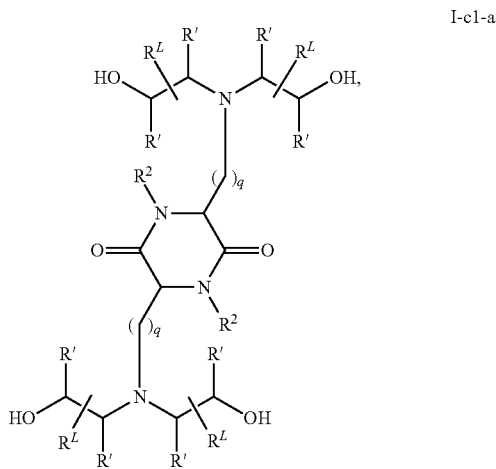

I-c1-a or a pharmaceutically acceptable salt thereof, wherein:

each $R^2$ independently is hydrogen or $C_{1-3}$ alkyl;

each q independently is 2 to 6;

each R' independently is hydrogen or $C_{1-3}$ alkyl;

and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

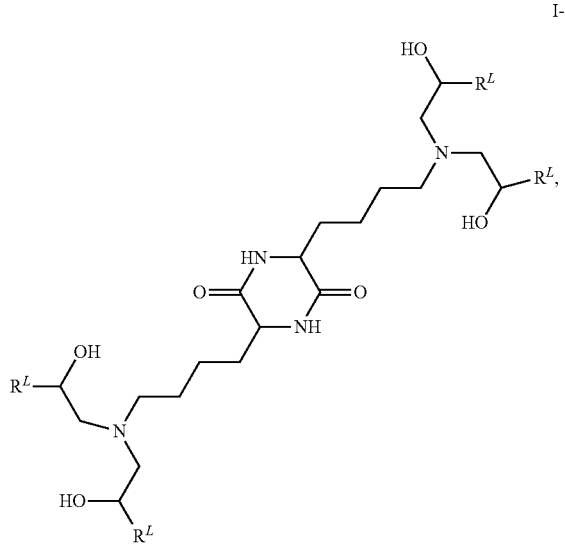

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). Structure of cKK-E12 is shown below:

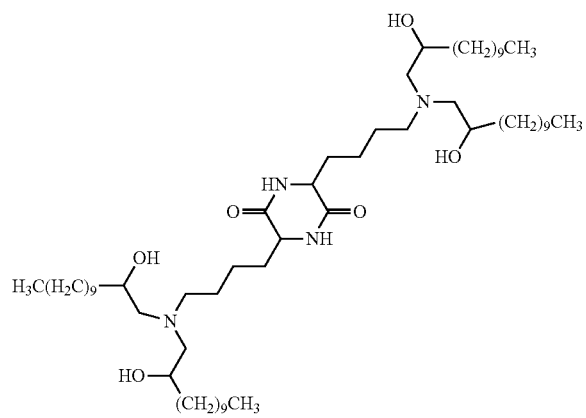

In some embodiments, the one or more cationic lipids may be N-[1-(2,3-dioleyloxy)propyl]-N,N,N-trimethylammonium chloride or "DOTMA". (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. No. 5,171,678; U.S. Pat. No. 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-1-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoley 1-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., cKK-E12) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEGylated lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thiouracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thiouracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., ASS1-encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., ASS1-encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., ASS1-encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., ASS1-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., ASS1-encoding mRNAs) include a 3' poly(A) tail structure. A poly-A tail on the 3' terminus of mRNA typically includes about 10 to 300 adenosine nucleotides (SEQ ID NO:9) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO:10) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer. Cap structure In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of m7G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m7G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m$^7$G(5')ppp(5')G ("m$^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of m$^7$GpppG, m$^7$GpppA, m$^7$GpppC; unmethylated cap analogs (e.g., GpppG); dimethylated cap analog (e.g., m$^{2,7}$GpppG), trimethylated cap analog (e.g., m$^{2,2,7}$GpppG), dimethylated symmetrical cap analogs (e.g., m$^7$Gpppm$^7$G), or anti reverse cap analogs (e.g., ARCA; m$^{7,2'Ome}$GpppG, m$^{72'd}$GpppG, m$^{7,3'Ome}$GpppG, m$^{73'd}$GpppG and their tetraphosphate derivatives) (see, e.g., Jemiility, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'-OCH$_3$ cap analogs (Jemiility, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides (SEQ ID NO: 11). In some embodiments, a poly-A tail on the 3' terminus of mRNA typically includes about 10 to 300 adenosine nucleotides (SEQ ID NO:9) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO:10) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer. Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Formation of Liposomes

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more lipisomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA encoding a ASS1 protein) described herein. Therapeutic agents can be administered at regular intervals, depending on the nature, severity and extent of the subject's condition (e.g., ASD). In some embodiments, a therapeutically effective amount of the therapeutic agents (e.g., mRNA encoding a ASS1 protein) of the present invention may be administered intrathecally periodically at regular intervals (e.g., once every year, once every six months, once every five months, once every three months, bimonthly (once every two months), monthly (once every month), biweekly (once every two weeks), once every 30 days, once every 28 days, once every 14 days, once every 10 days, once every 7 days, weekly, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In a preferred embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating ASD). For example, a therapeutically effective amount may be an amount sufficient to achieve a desired therapeutic and/or prophylactic effect. Generally, the amount of a therapeutic agent (e.g., mRNA encoding a ASS1 protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to the present invention, a therapeutically effective dose, when administered regularly, results in increased hepatic ASS1 levels. In some embodiments, a therapeutically effective dose, when administered regularly, results in reduced citrulline level in serum as compared to the baseline citrulline level before treatment. In some embodiments, a therapeutically effective dose, when administered regularly, results in reduced ammonia level in serum as compared to the baseline ammonia level before treatment.

In some embodiments, administering the provided composition results in increased expression of ASS1 protein in the liver as compared to baseline levels before the treatment. In some embodiment, administering the provided compositions results in an ASS1 protein level at or above about 3000 ng/mg, at or above about 2000 ng/mg, at or above about 1000 ng/mg, at or above about 500 ng/mg, at or above about 400 ng/mg, at or above about 200 ng/mg or at or above about 100 ng/mg of total protein in the liver. In a particular embodiment, administering the provided compositions results in an ASS1 protein level at or above 120 ng/mg of total protein in the liver.

In some embodiments, administering the provided composition results in increased ASS1 protein level in plasma or serum as compared to baseline level before the treatment. In some embodiments, administering the provided composition results in increased ASS1 protein level in plasma or serum by at least about 10%, 20%, 30%, 40%, 50%, 60%, 70%, 80%, 90%, or 95% as compared to baseline level before treatment.

In some embodiments, administering of the composition results in reduced citrulline and/or ammonia levels in the subject as compared to the baseline levels before treatment. Typically, the baseline levels are measured immediately before treatment. Typically, citrulline and/or ammonia levels are measured in a biological sample. Suitable biological samples include, for example, whole blood, plasma, serum, urine or cerebral spinal fluid.

In some embodiments, administering of the composition results in reduced citrulline level in a biological sample (e.g., a serum, plasma, or urine sample) by at least about 10%, 20%, 30%, 40%, 50%, 60%, 70%, 80%, 90%, or 95% as compared to the baseline citrulline level immediately before treatment. In some embodiments, administering of the composition results in reduced plasma citrulline level to less than about 2000 µM, 1500 µM, 1000 µM, 750 µM, 500 µM, 250 µM, 100 µM, 90 µM, 80 µM, 70 µM, 60 µM, 50 µM, 40 µM, or 30 µM.

In some embodiments, administering the composition results in reduced ammonia levels in a biological sample (e.g., a serum, plasma, or urine sample) by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline level immediately before treatment.

In some embodiments, administering the provided composition results in reduced ammonia levels in plasma or serum as compared to the baseline ammonia level immediately before treatment. In some embodiments, administering the provided composition results in reduced ammonia levels in plasma or serum as compared to the ammonia level in subjects who are not treated. In some embodiments, administering the composition results in reduction of ammonia levels to about 3000 µmol/L or less, about 2750 µmol/L or less, about 2500 µmol/L or less, about 2250 µmol/L or less, about 2000 µmol/L or less, about 1750 µmol/L or less, about 1500 µmol/L or less, about 1250 µmol/L or less, about 1000 µmol/L or less, about 750 µmol/L or less, about 500 µmol/L or less, about 250 µmol/L or less, about 100 µmol/L or less or about 50 µmol/L or less in the plasma or serum. In a particular embodiment, administering the composition results in reduction of ammonia levels to about 50 µmol/L or less in the plasma or serum.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable 1 week, two weeks, and/or 1 month after administration.

EXAMPLES

While certain compounds, compositions and methods of the present invention have been described with specificity in accordance with certain embodiments, the following examples serve only to illustrate the compounds of the invention and are not intended to limit the same.

Example 1

Exemplary Liposome Formulations for ASS1 mRNA Delivery and Expression

This example provides exemplary liposome formulations for effective delivery and expression of ASS1 mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding ASS1 protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (Semple, S. C. et al. "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), cKK-E12 (3,6-bis(4-(bis(2-hydroxydodecyl)amino)butyl)piperazine-2,5-dione), HGT5000, HGT5001, HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Codon-optimized human argininosuccinate synthetase (ASS1) messenger RNA was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length (SEQ ID NO:12) as determined by gel electrophoresis. 5' and 3' untranslated regions present in each mRNA product are represented as X and Y, respectively and defined as stated (vide infra).

Exemplary Codon-Optimized Human Argininosuccinate Synthetase (ASS1) mRNAs

Construct Design:

X—SEQ ID NO:3—Y;

X—SEQ ID NO:13—Y;

X—SEQ ID NO:14—Y; and

X—SEQ ID NO:15—Y.

5' and 3' UTR Sequences

[SEQ ID NO.: 4]
X (5' UTR Sequence) =
GGACAGAUCGCCUGGAGACGCCAUCCACGCUGUUUUGACCUCCAUAGAAG
ACACCGGGACCGAUCCAGCCUCCGCGGCCGGGAACGGUGCAUUGGAACGC
GGAUUCCCCGUGCCAAGAGUGACUCACCGUCCUUGACACG

[SEQ ID NO.: 5]
Y (3' UTR Sequence) =
CGGGUGGCAUCCCUGUGACCCCUCCCCAGUGCCUCUCCUGGCCCUGGAAG
UUGCCACUCCAGUGCCCACCAGCCUUGUCCUAAUAAAAUUAAGUUGCAUC
AAGCU

OR (SEQ ID NO.: 6)
GGGUGGCAUCCCUGUGACCCCUCCCCAGUGCCUCUCCUGGCCCUGGAAGU
UGCCACUCCAGUGCCCACCAGCCUUGUCCUAAUAAAAUUAAGUUGCAUCA
AGCU

Exemplary codon-optimized human ASS1 mRNA sequences include SEQ ID NO:3 described in the detailed description section, and SEQ ID NO:13, SEQ ID NO:14 and SEQ ID NO:15 below:

SEQ ID NO: 13
AUGAGCUCAAAGGGAUCUGUGGUGCUGGCAUACUCGGGGGGAUUGGACACUUCA
UGCAUACUUGUCUGGUUGAAGGAACAGGGCUACGACGUGAUCGCCUACCUGGCU
AACAUCGGUCAAAAGGAGGACUUCGAGGAGGCCCGGAAGAAGGCCCUGAAGCUG
GGCGCGAAGAAAGUGUUCAUCGAGGACGUGUCCCGGGAAUUUGUGGAAGAGUUC
AUCUGGCCCGCCAUCCAAAGCAGCGCACUGUACGAGGAUAGAUACCUCCUCGGAA
CAUCCCUUGCCCGGCCAUGUAUUGCCAGGAAACAGGUGGAAAUCGCCCAGCGGGA
AGGAGCCAAAUACGUGUCCCACGGGGCGACCGGAAAGGGGAACGACCAAGUGCGC
UUCGAGCUGUCGUGCUACUCCCUGGCACCGCAGAUUAAGGUCAUCGCGCCGUGGA
GAAUGCCUGAAUUCUACAACCGCUUCAAGGGCCGCAACGAUCUGAUGGAAUACGC
CAAGCAGCACGGCAUCCCGAUCCCCGUGACCCCUAAGAACCCUUGGUCAAUGGAC
GAGAAUCUGAUGCACAUCAGCUACGAAGCGGGCAUCCUGGAGAACCCCAAGAAUC
AAGCUCCGCCCGGACUGUACACUAAGACUCAGGAUCCCGCUAAGGCGCCCAACAC
UCCUGAUAUUUUGGAAAUCGAAUUCAAGAAGGGUGUCCCAGUGAAGGUCACCAA
CGUGAAGGACGGCACUACCCACCAGACCUCGCUGGAACUGUUUAUGUAUCUGAAC
GAGGUGGCCGGCAAACAUGGAGUCGGCAGAAUCGAUAUUGUGGAGAACCGCUUU
AUUGGCAUGAAGUCCAGGGGGAUCUAUGAAACCCCGGCCGGAACCAUCCUCUACC
ACGCCCAUCUCGACAUUGAAGCGUUCACCAUGGACCGCGAGGUCCGCAAGAUUAA
GCAGGGCCUGGGACUCAAGUUCGCCGAGCUCGUGUACACCGGUUUCUGGCAUUCC
CCGGAAUGCGAAUUCGUGCGACACUGCAUUGCCAAGAGCCAGGAGCGGGUGGAA
GGAAAGGUCCAGGUGUCCGUGCUGAAGGGUCAAGUGUACAUCCUGGGGCGGGAG
UCCCCUCUUUCCCUGUACAACGAAGAACUGGUGUCGAUGAACGUGCAGGGAGACU
ACGAGCCGACCGACGCCACGGGUUUCAUUAACAUCAAUUCCCUGAGACUGAAGGA
GUACCACCGGCUCCAGUCCAAAGUCACCGCUAAGUGA (SEQ ID NO: 13),

SEQ ID NO: 14
AUGAGCUCAAAAGGAUCGGUGGUGCUGGCAUACUCGGGAGGAUUGGACACUUCA
UGUAUUCUUGUCUGGCUCAAGGAACAGGGCUACGACGUCAUUGCCUACCUGGCCA
ACAUCGGUCAGAAAGAGGACUUCGAGGAAGCCAGAAAGAAGGCCCUGAAGCUGG
GAGCCAAGAAGGUGUUCAUCGAGGACGUGUCCCGCGAAUUUGUGGAAGAAUUCA
UCUGGCCCUGCCAUUCAAUCCUCCGCGCUCUACGAGGAUCGGUACCUUCUGGGAAC
UUCCUUGGCUCGCCCGUGCAUCGCCCGGAAACAAGUGGAGAUUGCACAGCGGGAA
GGAGCUAAGUACGUGUCCCACGGGGCCACUGGAAAGGGCAACGAUCAAGUGCGCU

-continued

UCGAGCUGUCCUGCUACUCCCUGGCGCCACAGAUCAAGGUCAUCGCGCCGUGGCG

GAUGCCCGAGUUCUAUAACCGCUUCAAGGGACGGAACGAUCUGAUGGAGUACGCC

AAGCAGCACGGCAUUCCGAUACCCGUGACCCCCAAGAACCCUUGGAGCAUGGACG

AGAACCUGAUGCAUAUCUCUUACGAAGCCGGGAUUCUCGAAAACCCUAAGAAUCA

GGCGCCGCCUGGCCUGUACACCAAAACCCAGGACCCCGCCAAGGCGCCGAACACG

CCCGACAUCCUCGAAAUCGAGUUCAAGAAGGGGUGCCAGUGAAGGUCACCAACG

UGAAGGACGGAACCACCCAUCAGACCUCACUGGAACUCUUCAUGUACCUCAACGA

GGUCGCAGGGAAGCACGGCGUGGGGAGAAUCGACAUCGUGGAAAACAGGUUCAU

CGGCAUGAAGUCCCGGGGAAUCUACGAAACACCCGCCGGGACUAUCCUCUACCAC

GCCCACCUGGACAUUGAGGCCUUCACCAUGGAUAGAGAAGUGCGCAAGAUUAAGC

AGGGUCUGGGUCUGAAGUUCGCCGAGUUGGUCUACACCGGAUUCUGGCAUUCCCC

UGAAUGCGAAUUCGUGCGCCACUGCAUUGCCAAGAGCCAGGAAAGAGUGGAGGG

CAAAGUCCAAGUGUCGGUGCUGAAGGGCCAAGUGUACAUCCUGGGAAGGGAAAG

CCCGCUCUCCCUGUACAACGAGGAACUGGUGUCGAUGAACGUCCAGGGCGAUUAU

GAGCCGACUGACGCCACUGGUUUUAUCAAUAUCAACAGCCUGCGACUGAAGGAGU

ACCACCGGCUGCAGUCCAAGGUCACCGCUAAGUAG (SEQ ID NO: 14),

SEQ ID NO: 15
AUGAGCUCGAAAGGAUCCGUGGUUUUGGCAUACUCCGGUGGACUUGACACUUCA

UGCAUUUUGGUUUGGCUCAAAGAACAGGGCUACGAUGUGAUCGCCUACCUGGCG

AACAUCGGACAGAAAGAGGACUUUGAAGAGGCCCGCAAGAAGGCACUGAAGCUG

GGUGCCAAGAAAGUGUUUAUCGAGGAUGUGUCGAGAGAAUUCGUGGAAGAAUUC

AUUUGGCCAGCCAUUCAAAGCUCCGCGCUGUACGAGGACAGAUACCUCCUCGGCA

CCUCACUGGCCCGCCCUUGCAUCGCGCGCAAACAGGUCGAGAUCGCUCAAAGAGA

AGGAGCUAAAUACGUGUCACACGGCGCCACCGGAAAGGGAAAUGACCAAGUCCGC

UUCGAGCUGUCUUGCUACUCACUCGCUCCGCAAAUCAAGGUCAUCGCACCGUGGA

GGAUGCCCGAGUUCUACAACCGGUUCAAGGGGCGGAACGACCUGAUGGAGUACGC

GAAGCAGCACGGUAUCCCGAUCCCUGUCACCCCAAAGAACCCCUGGAGCAUGGAC

GAAAAUCUGAUGCACAUCAGCUACGAAGCAGGAAUCCUGGAGAACCCGAAAAAU

CAAGCACCUCCUGGACUGUACACUAAGACCCAGGACCCAGCCAAGGCCCCGAAUA

CCCCGGACAUCUUGGAAAUCGAGUUCAAGAAGGGGGUGCCAGUGAAGGUUACCA

AUGUCAAGGAUGGGACCACUCACCAAACUAGCCUGGAACUGUUCAUGUACCUGAA

CGAAGUGGCUGGAAAACAUGGCGUGGGAAGAAUCGAUAUCGUGGAGAACCGCUU

CAUCGGCAUGAAGUCAAGGGGAAUCUACGAAACUCCGGCCGGGACGAUACUGUA

UCAUGCGCAUCUCGACAUUGAAGCCUUUACUAUGGAUCGGGAAGUCCGAAAGAU

CAAACAGGGCUUGGGCCUCAAGUUUGCCGAGCUGGUGUACACGGGAUUCUGGCAC

UCGCCGGAAUGCGAAUUCGUGCGCCACUGUAUUGCGAAGUCCCAGGAGCGCGUGG

AAGGGAAGGUCCAAGUCUCCGUGCUCAAAGGACAGGUCUACAUCCUUGGACGGG

AGUCGCCCUGUCGCUCUACAACGAAGAACUGGUGUCGAUGAACGUGCAGGGAGA

CUAUGAACCAACGGAUGCUACUGGUUUCAUCAACAUCAAUUCGCUGCGGCUUAAG

GAGUACCAUCGGCUGCAGUCCAAGGUCACCGCGAAGUAG(SEQ ID NO: 15).

An exemplary full-length codon-optimized human argininosuccinate synthetase (ASS1) messenger RNA sequence is shown below:

(SEQ ID NO: 7)

```
GGACAGAUCGCCUGGAGACGCCAUCCACGCUGUUUUGACCUCCAUAGAAGACACC
GGGACCGAUCCAGCCUCCGCGGCCGGGAACGGUGCAUUGGAACGCGGAUUCCCCG
UGCCAAGAGUGACUCACCGUCCUUGACACGAUGAGCAGCAAGGGCAGCGUGGUGC
UGGCCUACAGCGGCGGCCUGGACACCAGCUGCAUCCUGGUGUGGCUGAAGGAGCA
GGGCUACGACGUGAUCGCCUACCUGGCCAACAUCGGCCAGAAGGAGGACUUCGAG
GAGGCCCGCAAGAAGGCCCUGAAGCUGGGCGCCAAGAAGGUGUUCAUCGAGGACG
UGAGCCGCGAGUUCGUGGAGGAGUUCAUCUGGCCCGCCAUCCAGAGCAGCGCCCU
GUACGAGGACCGCUACCUGCUGGGCACCAGCCUGGCCCGCCCCUGCAUCGCCCGC
AAGCAGGUGGAGAUCGCCCAGCGCGAGGGCGCCAAGUACGUGAGCCACGGCGCCA
CCGGCAAGGGCAACGACCAGGUGCGCUUCGAGCUGAGCUGCUACAGCCUGGCCCC
CCAGAUCAAGGUGAUCGCCCCCUGGCGCAUGCCCGAGUUCUACAACCGCUUCAAG
GGCCGCAACGACCUGAUGGAGUACGCCAAGCAGCACGGCAUCCCCAUCCCCGUGA
CCCCCAAGAACCCCUGGAGCAUGGACGAGAACCUGAUGCACAUCAGCUACGAGGC
CGGCAUCCUGGAGAACCCCAAGAACCAGGCCCCCCCGGCCUGUACACCAAGACC
CAGGACCCCGCCAAGGCCCCCAACACCCCCGACAUCCUGGAGAUCGAGUUCAAGA
AGGGCGUGCCCGUGAAGGUGACCAACGUGAAGGACGGCACCACCCACCAGACCAG
CCUGGAGCUGUUCAUGUACCUGAACGAGGUGGCCGGCAAGCACGGCGUGGGCCGC
AUCGACAUCGUGGAGAACCGCUUCAUCGGCAUGAAGAGCCGCGGCAUCUACGAGA
CCCCCGCCGGCACCAUCCUGUACCACGCCCACCUGGACAUCGAGGCCUUCACCAUG
GACCGCGAGGUGCGCAAGAUCAAGCAGGGCCUGGGCCUGAAGUUCGCCGAGCUGG
UGUACACCGGCUUCUGGCACAGCCCCGAGUGCGAGUUCGUGCGCCACUGCAUCGC
CAAGAGCCAGGAGCGCGUGGAGGGCAAGGUGCAGGUGAGCGUGCUGAAGGGCCA
GGUGUACAUCCUGGGCCGCGAGAGCCCCCUGAGCCUGUACAACGAGGAGCUGGUG
AGCAUGAACGUGCAGGGCGACUACGAGCCCACCGACGCCACCGGCUUCAUCAACA
UCAACAGCCUGCGCCUGAAGGAGUACCACCGCCUGCAGAGCAAGGUGACCGCCAA
GUGACGGGUGGCAUCCCUGUGACCCCUCCCCAGUGCCUCUCCUGGCCCUGGAAGU
UGCCACUCCAGUGCCCACCAGCCUUGUCCUAAUAAAAUUAAGUUGCAUCAAGCU.
```

In another example, a full length codon-optimized human argininosuccinate synthetase (ASS1) messenger RNA sequence is shown below:

(SEQ ID NO: 8)

```
GGACAGAUCGCCUGGAGACGCCAUCCACGCUGUUUUGACCUCCAUAGAAGACACC
GGGACCGAUCCAGCCUCCGCGGCCGGGAACGGUGCAUUGGAACGCGGAUUCCCCG
UGCCAAGAGUGACUCACCGUCCUUGACACGAUGAGCAGCAAGGGCAGCGUGGUGC
UGGCCUACAGCGGCGGCCUGGACACCAGCUGCAUCCUGGUGUGGCUGAAGGAGCA
GGGCUACGACGUGAUCGCCUACCUGGCCAACAUCGGCCAGAAGGAGGACUUCGAG
GAGGCCCGCAAGAAGGCCCUGAAGCUGGGCGCCAAGAAGGUGUUCAUCGAGGACG
UGAGCCGCGAGUUCGUGGAGGAGUUCAUCUGGCCCGCCAUCCAGAGCAGCGCCCU
```

-continued

```
GUACGAGGACCGCUACCUGCUGGGCACCAGCCUGGCCCGCCCCUGCAUCGCCCGC

AAGCAGGUGGAGAUCGCCCAGCGCGAGGGCGCCAAGUACGUGAGCCACGGCGCCA

CCGGCAAGGGCAACGACCAGGUGCGCUUCGAGCUGAGCUGCUACAGCCUGGCCCC

CCAGAUCAAGGUGAUCGCCCCCUGGCGCAUGCCCGAGUUCUACAACCGCUUCAAG

GGCCGCAACGACCUGAUGGAGUACGCCAAGCAGCACGGCAUCCCCAUCCCCGUGA

CCCCCAAGAACCCCUGGAGCAUGGACGAGAACCUGAUGCACAUCAGCUACGAGGC

CGGCAUCCUGGAGAACCCCAAGAACCAGGCCCCCCCCGGCCUGUACACCAAGACC

CAGGACCCCGCCAAGGCCCCCAACACCCCCGACAUCCUGGAGAUCGAGUUCAAGA

AGGGCGUGCCCGUGAAGGUGACCAACGUGAAGGACGGCACCACCCACCAGACCAG

CCUGGAGCUGUUCAUGUACCUGAACGAGGUGGCCGGCAAGCACGGCGUGGGCCGC

AUCGACAUCGUGGAGAACCGCUUCAUCGGCAUGAAGAGCCGCGGCAUCUACGAGA

CCCCCGCCGGCACCAUCCUGUACCACGCCCACCUGGACAUCGAGGCCUUCACCAUG

GACCGCGAGGUGCGCAAGAUCAAGCAGGGCCUGGGCCUGAAGUUCGCCGAGCUGG

UGUACACCGGCUUCUGGCACAGCCCCGAGUGCGAGUUCGUGCGCCACUGCAUCGC

CAAGAGCCAGGAGCGCGUGGAGGGCAAGGUGCAGGUGAGCGUGCUGAAGGGCCA

GGUGUACAUCCUGGGCCGCGAGAGCCCCCUGAGCCUGUACAACGAGGAGCUGGUG

AGCAUGAACGUGCAGGGCGACUACGAGCCCACCGACGCCACCGGCUUCAUCAACA

UCAACAGCCUGCGCCUGAAGGAGUACCACCGCCUGCAGAGCAAGGUGACCGCCAA

GUGAGGGUGGCAUCCCUGUGACCCCUCCCCAGUGCCUCUCCUGGCCCUGGAAGUU

GCCACUCCAGUGCCCACCAGCCUUGUCCUAAUAAAAUUAAGUUGCAUCAAAGCU.
```

Exemplary Formulation Protocols

A. cKK-E12

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.64 mg/mL ASS1 mRNA (encapsulated). $Z_{ave}$=78 nm ($Dv_{(50)}$)=46 nm; $Dv_{(90)}$=96 nm).

B. C12-200

Aliquots of 50 mg/mL ethanolic solutions of C12-200, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.82 mg/mL ASS1 mRNA (encapsulated). $Z_{ave}$=86 nm ($Dv_{(50)}$=50 nm; $Dv_{(90)}$=101 nm).

C. HGT4003

Aliquots of 50 mg/mL ethanolic solutions of HGT4003, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.82 mg/mL ASS1 mRNA (encapsulated). $Z_{ave}$=86 nm ($Dv_{(50)}$=50 nm; $Dv_{(90)}$=101 nm).

D. ICE

Aliquots of 50 mg/mL ethanolic solutions of ICE, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.91 mg/mL ASS1 mRNA (encapsulated). $Z_{ave}$=81 nm ($Dv_{(50)}$=48 nm; $Dv_{(90)}$=96 nm).

E. HGT5001

Aliquots of 50 mg/mL ethanolic solutions of HGT5001, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL ASS1 mRNA (encapsulated). $Z_{ave}$=87.0 nm ($Dv_{(50)}$=75 nm; $Dv_{(90)}$=103 nm).

F. HGT5000

Aliquots of 50 mg/mL ethanolic solutions of HGT5000, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL ASS1 mRNA (encapsulated). Zave=81 nm ($Dv_{(50)}$=67 nm; $Dv_{(90)}$=97 nm).

G. DLinKC2DMA

Aliquots of 50 mg/mL ethanolic solutions of DLinKC2DMA, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL ASS1 mRNA (encapsulated). Zave=78 nm ($Dv_{(50)}$=60 nm; $Dv_{(90)}$=92 nm).

H. DODAP

Aliquots of 50 mg/mL ethanolic solutions of DODAP, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL ASS1 mRNA (encapsulated). Zave=84 nm ($Dv_{(50)}$=62 nm; $Dv_{(90)}$=92 nm).

I. DODMA

Aliquots of 50 mg/mL ethanolic solutions of DODMA, DOPE, cholesterol and DMG-PEG2K were mixed and diluted with ethanol to 3 mL final volume. Separately, an aqueous buffered solution (10 mM citrate/150 mM NaCl, pH 4.5) of ASS1 mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.20 mg/mL ASS1 mRNA (encapsulated). Zave=86 nm ($Dv_{(50)}$=69 nm; $Dv_{(90)}$=98 nm).

Example 2

Administration of ASS1 mRNA-Loaded Liposome Nanoparticles

This example illustrates exemplary methods of administering ASS1 mRNA-loaded liposome nanoparticles and methods for analyzing expressed protein in various target tissues in vivo.

All studies were performed using male CD-1 mice of approximately 6-8 weeks of age at the beginning of each experiment. Samples were introduced by a single bolus tail-vein injection of an equivalent total dose of 1.0 mg/kg (or otherwise specified) of encapsulated ASS1 mRNA. Mice were sacrificed and perfused with saline at the designated time points.

Tissues such as liver, spleen, kidney and heart of each mouse were harvested, apportioned into separate parts, and stored in either 10% neutral buffered formalin or snap-frozen and stored at −80° C. for analysis.

All animals were euthanized by $CO_2$ asphyxiation at designated time points post dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collections, approximately 40-50 μL of whole blood was collected via facial vein puncture or tail snip. Samples collected from non-treatment animals were used as baseline ASS1 levels for comparison to study animals.

Enzyme-Linked Immunosorbent Assay (ELISA) Analysis— Human ASS1 ELISA

Standard ELISA procedures were followed employing mouse anti-ASS1 2D1-2E12 IgG as the capture antibody with rabbit anti-ASS1 #3285 IgG as the secondary (detection) antibody (Shire Human Genetic Therapies). Horseradish peroxidase (HRP)-conjugated goat anti-rabbit IgG was used for activation of the 3,3',5,5'-tetramethylbenzidine (TMB) substrate solution. The reaction was quenched using $2NH_2SO_4$ after 20 minutes. Detection was monitored via absorption (450 nm) on a Molecular Device SpectraMax instrument. Untreated mouse serum and organs and human ASS1 protein were used as negative and positive controls, respectively.

Example 3

Efficient ASS1 Protein Expression In Vivo

This example demonstrates that administration of ASS1 mRNA results in successful protein production and clinical efficacy in vivo.

The production of human ASS1 protein via codon-optimized hASS1 mRNA-loaded lipid nanoparticles was tested in CD-1 mice as a single, bolus intravenous injection. FIG. 1 represents the amount of human ASS1 protein detected via ELISA when mice were treated with human ASS1 mRNA-loaded cKK-E12-based lipid nanoparticles at various doses. The mice were sacrificed twenty-four hours post-injection and organs were harvested (as described above).

As shown in FIG. 1, a clear dose response was achieved when measuring liver levels of human ASS1 protein. The dosing range was from 0.10-2.0 mg/kg of encapsulated human ASS1 mRNA. These data demonstrate the ability of the lipid nanoparticles to accumulate in the liver and release the mRNA payload and the liver to process this exogenous mRNA via translation to produce human ASS1 protein. Raw values of human ASS1 protein as measured via ELISA analysis (as depicted in FIG. 1) were shown in Table 1 below.

TABLE 1

| Dose Encapsulated ASS1 mRNA (mg/kg) | Human ASS1 Protein (ng/mg total protein) |
|---|---|
| 0.10 | BLD |
| 0.30 | BLD |

TABLE 1-continued

| Dose Encapsulated ASS1 mRNA (mg/kg) | Human ASS1 Protein (ng/mg total protein) |
|---|---|
| 0.60 | 546 |
| 1.0 | 1388 |
| 2.0 | 3371 |

Codon-optimized human ASS1 mRNA was delivered via cKK-E12-based lipid nanoparticles. Doses are based on encapsulated ASS1 mRNA. Values are depicted as nanogram of human ASS1 protein per milligram total protein in liver. BLD=Below Limit of Detection for ELISA.

While the sensitivity of the ELISA has limitations at lower values, western blot analysis allows for clear visualization of the human ASS1 protein at lower doses (0.30 mg/kg) (FIGS. 2A-2D).

Figure 3:
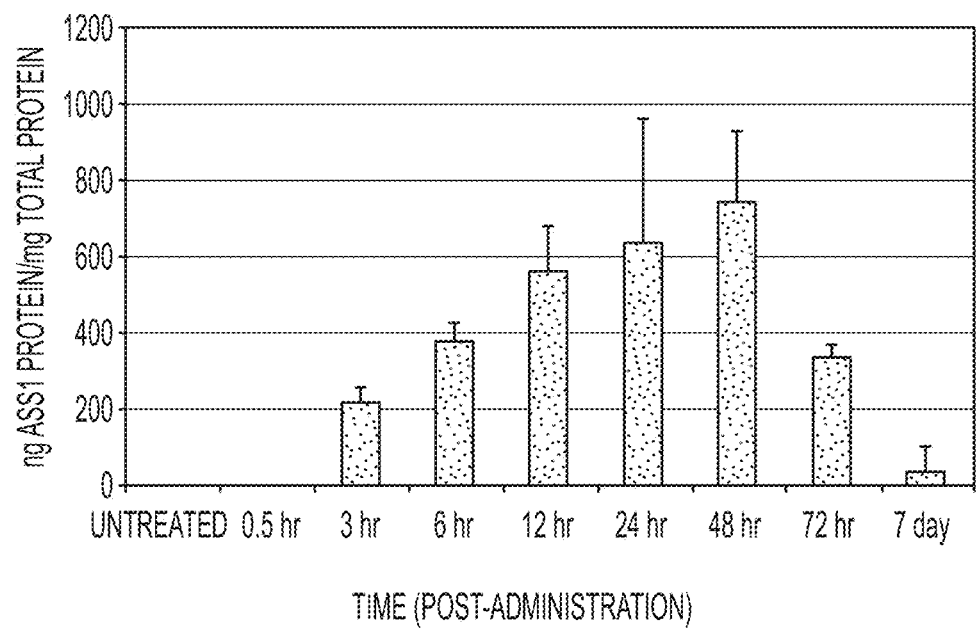
FIG. 3 depicts an exemplary graph of accumulated human argininosuccinate synthetase (ASS1) protein levels as measured via ELISA. The protein detected was a result of its production from ASS1 mRNA delivered intravenously via a single dose of lipid nanoparticles (1.0 mg/kg encapsulated ASS1 mRNA) over time.
Figure 4A:
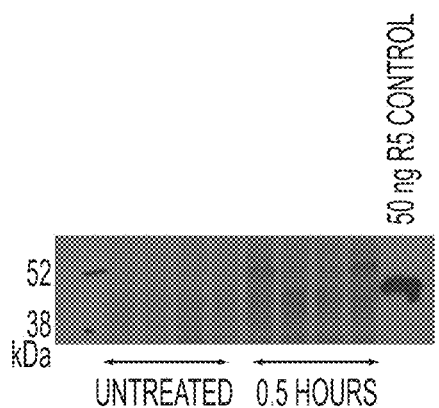
FIGS. 4A-4E depict exemplary Western blots of human ASS1 protein levels in liver over time after a single intravenous dose of human ASS1 mRNA-encapsulated lipid nanoparticles (1.0 mg/kg dose).
Figure 4B:
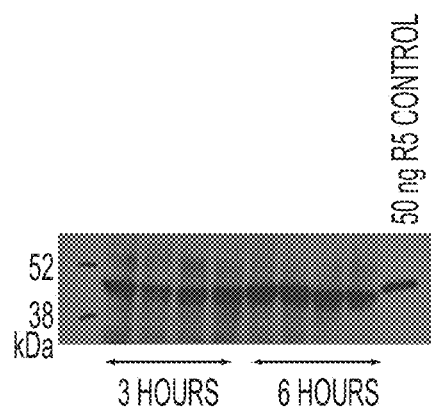
Figures 4C, 4D, 4E:
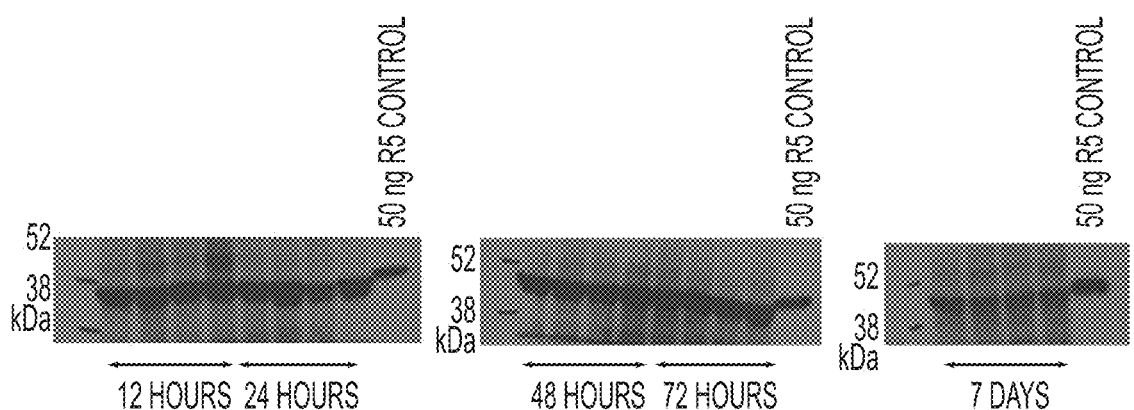
Figure 5A:
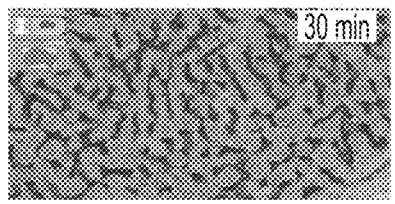
FIGS. 5A-5I depict detection of human ASS1 messenger RNA via in situ hybridization in the livers of treated mice. Exogenous mRNA is observable for at least 7 days post-administration after a single dose (1.0 mg/kg) of ASS1 mRNA-loaded cKK-E12-based lipid nanoparticles. Human ASS1 mRNA is detectable in sinusoidal cells as well as hepatocytes.
Figure 5B:
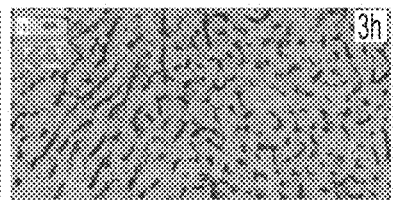
Figure 5C:
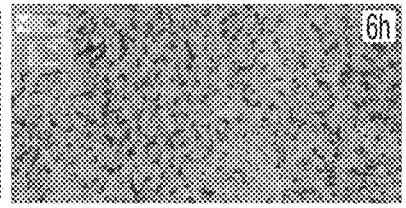
Figure 5D:
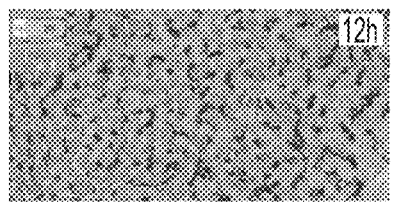
Figure 5E:
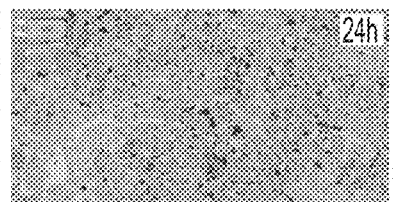
Figure 5F:
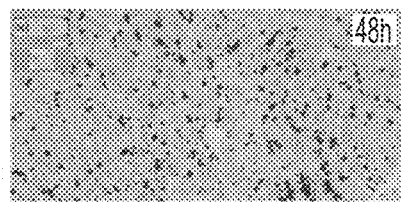
Figure 5G:
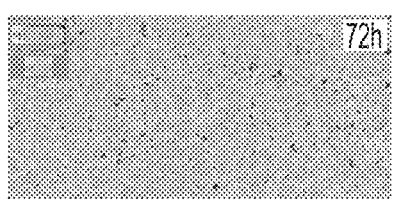
Figure 5H:
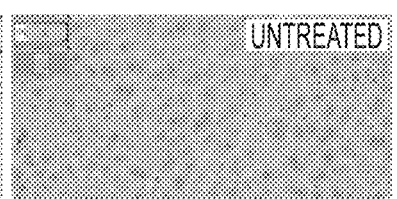
Figure 5I:
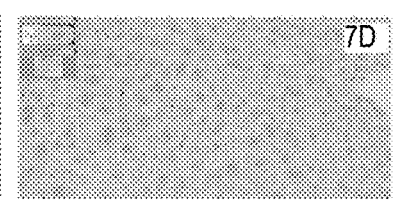
Figure 6A:
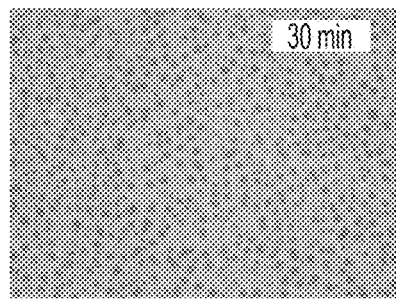
FIGS. 6A-6I depict exemplary immunohistochemical staining of ASS1 protein levels in mouse liver at various time points after administration of 1 mg/kg ASS1 mRNA containing cKK-E12 lipid nanoparticles. Human ASS1 protein is detectable in sinusoidal cells as well as hepatocytes. Human ASS1 protein is detectable for at least one week post-administration of a single dose of ASS1 mRNA-loaded lipid nanoparticles.
Figure 6B:
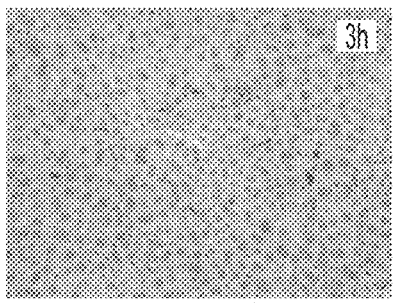
Figure 6C:
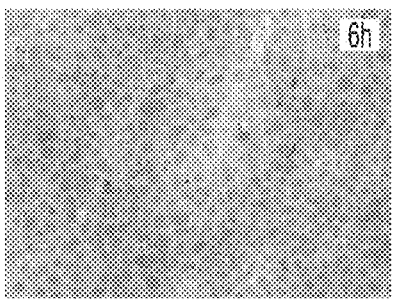
Figure 6D:
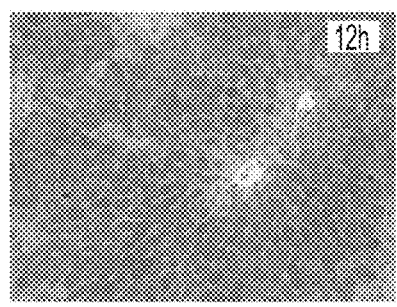
Figure 6E:
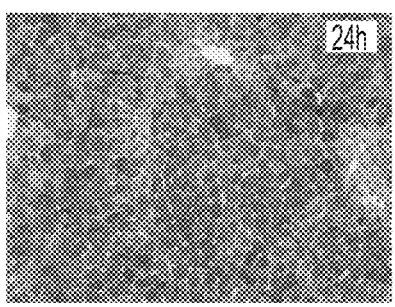
Figure 6F:
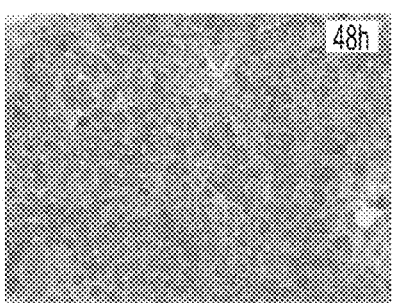
Figure 6G:
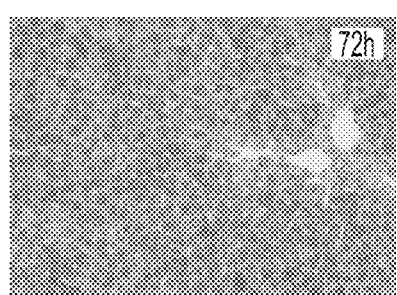
Figure 6H:
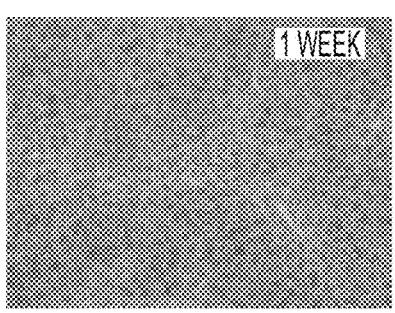
Figure 6I:
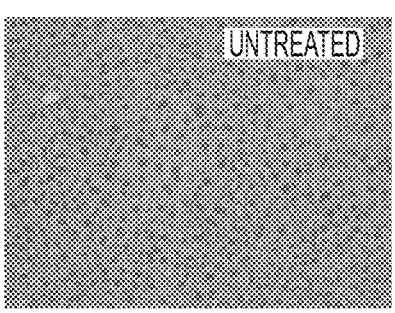

To further understand the ability of ASS1 mRNA-encapsulated lipid nanoparticles to facilitate the delivery of mRNA to selected organs (liver), we pursued a pharmacokinetic study monitoring human ASS1 protein levels in the liver over a one week time period. FIG. 3 depicts the quantity of human ASS1 protein detected in the liver at various time points after administration of human ASS1-loaded lipid nanoparticles (cKK-E12). This was accomplished as a single dose (1.0 mg/kg encapsulated mRNA) given intravenously.

In this case we observed a maximum serum level of human ASS1 protein at approximately 24-48 hours post-administration. Measurable levels of protein were still observed 1 week post-administration as determined by both ELISA and western blot (FIGS. 3 and 4A-4E, respectively).

Direct detection of the active pharmaceutical ingredient (ASS1 mRNA) in the livers of the treated mice was achieved using in situ hybridization (ISH) based methods. As demonstrated in FIGS. 5A-5I, the exogenous human ASS1 messenger RNA could be detected in high levels at the earliest time point tested (30 minutes) and the signal remained strong for 48 hours after dosing. Further, human ASS1 mRNA was still detectable 7 days post-administration.

In addition to ISH, detection of the resulting human ASS1 protein was achieved using immunohistochemical (IHC) means. Using a mouse monoclonal antibody (02D2-2E12) for specific binding, we readily observed the target human ASS1 protein in the cytoplasm of hepatocytes of treated livers. The signal was first observed in treated livers faintly within 30 minutes but clearly within 3 hours post-administration. FIGS. 6A-6I show the staining of human ASS1 protein in treated mouse livers as a function of time after administration.

Figure 7A:
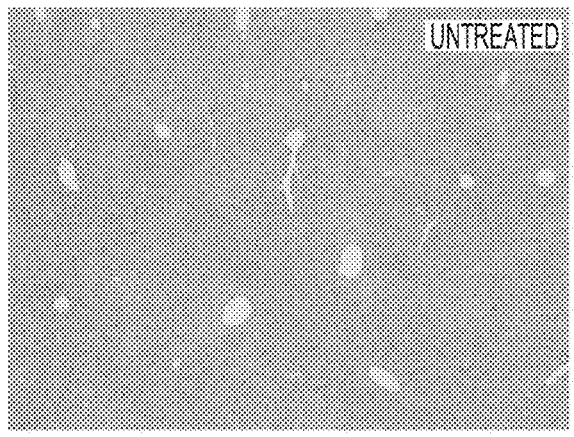
FIGS. 7A-7B depict low magnification (4×) immunohistochemical staining of ASS1 protein levels in mouse liver 24 hours after administration of 1 mg/kg ASS1 mRNA-containing cKK-E12 liposomes. A comparison to untreated mouse liver (left) demonstrates the widespread distribution of human ASS1 protein throughout the liver.
Figure 7B:
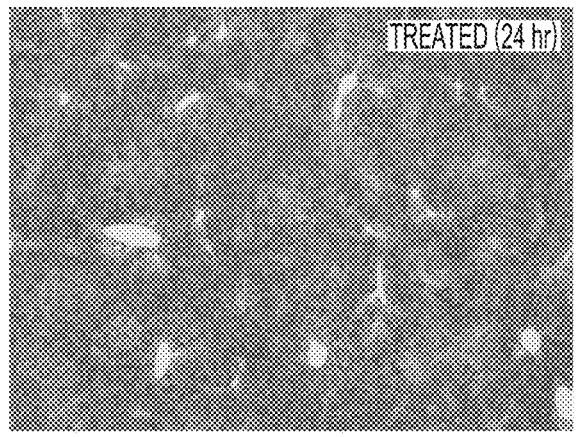

Further, one observes widespread distribution throughout the liver with strong detection of human ASS1 protein in both the sinusoidal cells as well as the target hepatocyte cells. FIGS. 7A-7B represent a low magnification representation of positive IHC staining for human ASS1 protein 24 hours post-administration.

Figure 8:
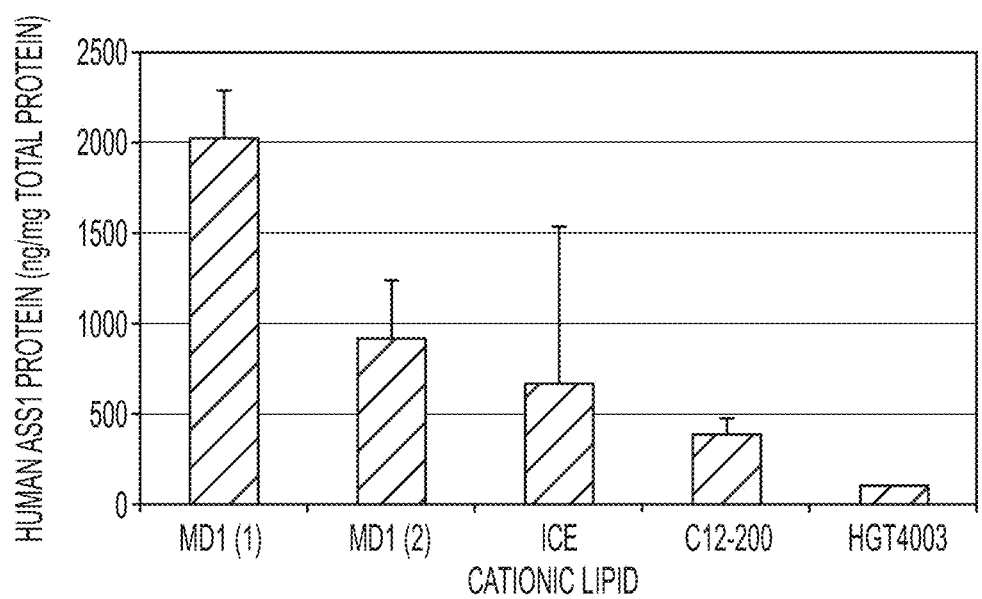
FIG. 8 depicts an exemplary graph of human argininosuccinate synthetase (ASS1) protein levels as measured via ELISA. The protein detected was a result of its production from ASS1 mRNA delivered intravenously via a single dose of various lipid nanoparticles.

The delivery of human ASS1 mRNA and subsequent protein production is not limited to a single lipid nanoparticle system. Several cationic lipid-based nanoparticle systems were explored for their ability to deliver mRNA and produce the desired protein. A screen of 10 different cationic lipid systems was investigated using human ASS1 mRNA as the analyte of choice. The cationic lipid component for each formulation is listed in Table 2 as well as depicted in FIG. 8. Single, intravenous injections were administered and liver samples were taken 24 hours post-administration.

Doses of formulations were all 1.0 mg/kg based on encapsulated mRNA Values are based on liver samples 24 hours post-administration.

TABLE 2

| Cationic/Ionizable Lipid Component | Dose (mg/kg) | Human ASS1 Protein (ng/mg total protein) |
|---|---|---|
| cKK-E12 (1) | 1.0 | 2,028 |
| cKK-E12 (2) | 1.0 | 911 |
| ICE | 1.0 | 663 |
| C12-200 | 1.0 | 385 |
| HGT4003 | 1.0 | 100 |

Figure 9:
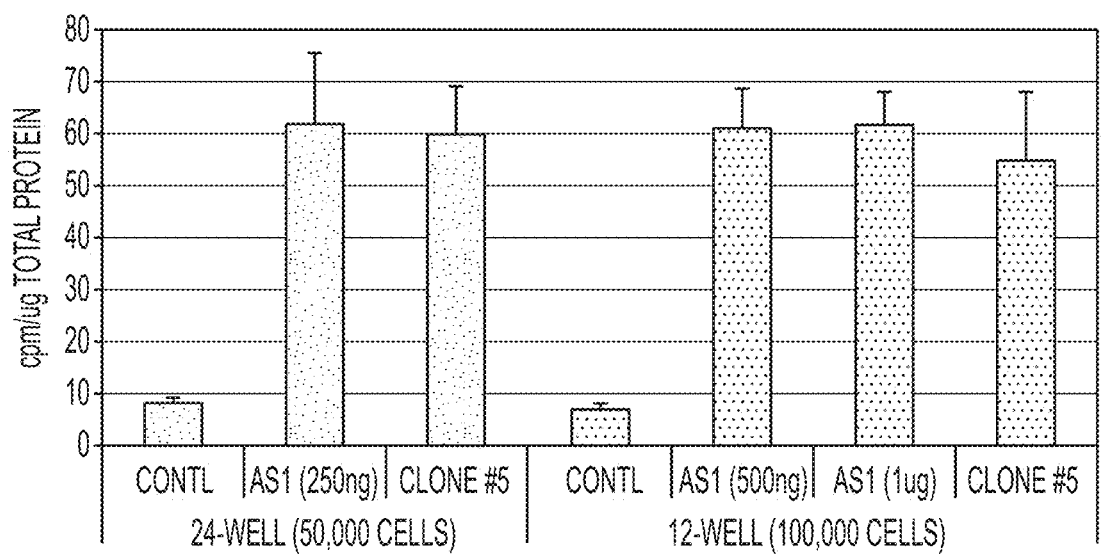
FIG. 9 depicts $^{14}C$ Arginine incorporation into proteins after transfection of ASS1 mRNA in an ASS1 KO cell line (SK (−)) as compared to a stably-expressing positive AS1 cell line (SK (+), Clone #5). Control represents lipofectamine-only treated SK (−) cells.

Raw values of human ASS1 protein for various cationic lipid-based nanoparticle systems as measured via ELISA analysis (as depicted in FIG. 9). All doses were administered intravenously at 1.0 mg/kg. Values of protein are depicted as nanogram of human ASS1 protein per milligram of total liver protein. cKK-E12 (1) has a lower percentage of PEG lipid than cKK-E12 (2) (3% vs 5% PEG lipid).

While the production of protein via mRNA-loaded lipid nanoparticles can be detected, we further determined if the resulting protein is active and can function properly. To this end, in vitro activity studies were conducted which measured incorporation of $^{14}C$ arginine into cellular proteins via supplementation of $^{14}C$ citrulline. The radioactive citrulline was converted to $^{14}C$-argininosuccinate, and subsequently to $^{14}C$-arginine, in the presence of active ASS1 protein. By comparing human ASS1 mRNA transfected cells versus untreated cells, we could gauge the activity of the respective exogenous mRNA-derived ASS1 protein. FIG. 9 represents radioactive counts per minute of $^{14}C$ arginine incorporation into cellular proteins. Transfection of SK (−) cells (ASS1 protein knockout cell line) with human ASS1 mRNA exposed to depleted media (no arginine or leucine) resulted in an increase in observed radioactivity as compared to untreated SK(−) cells. Activity measured in these transfected cells was comparable to a stably-transfected positive ASS1 cell line (SK (+)).

Example 4

Human ASS1 Protein Levels Following Treatment with ASS1 mRNA-Loaded Lipid Nanoparticles This example demonstrates that administration of ASS1 mRNA results in successful production of ASS1 protein in the liver.

Figure 10:
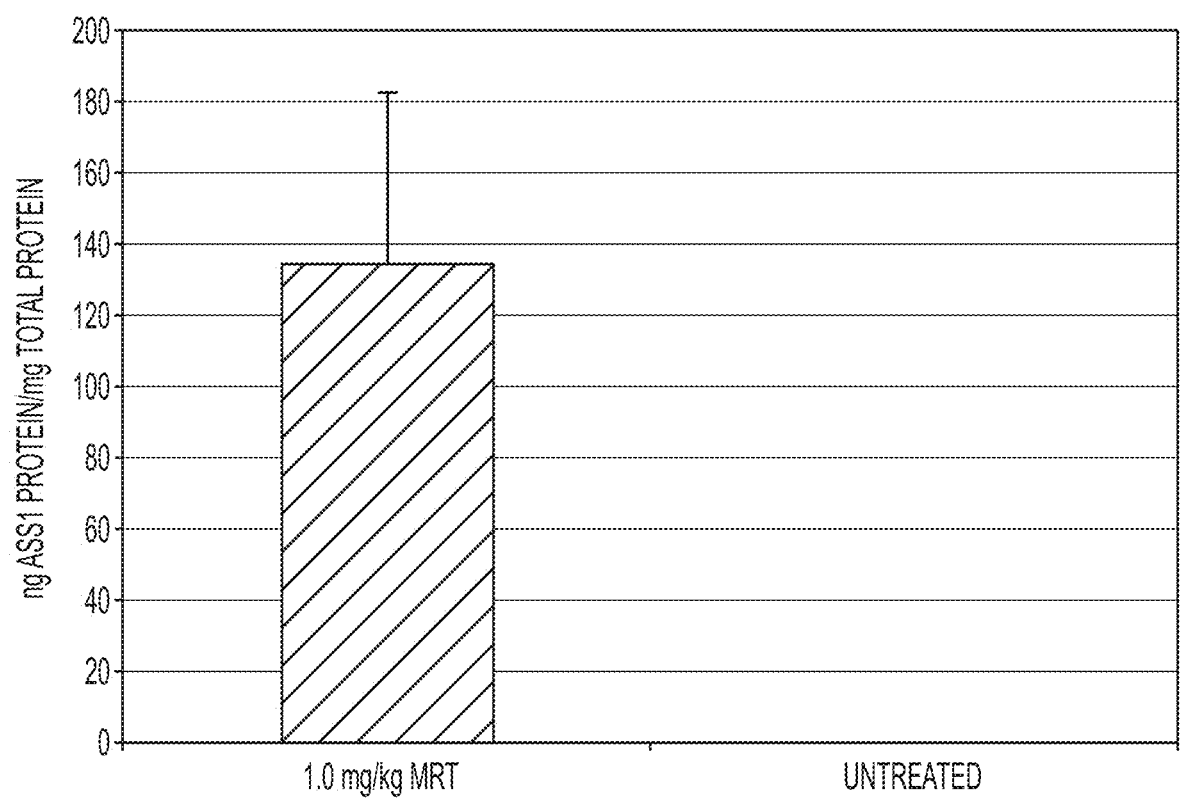
FIG. 10 depicts human ASS1 protein levels in rat liver 24 hours after administration of ASS1 mRNA-loaded lipid nanoparticles.
Figure 11:
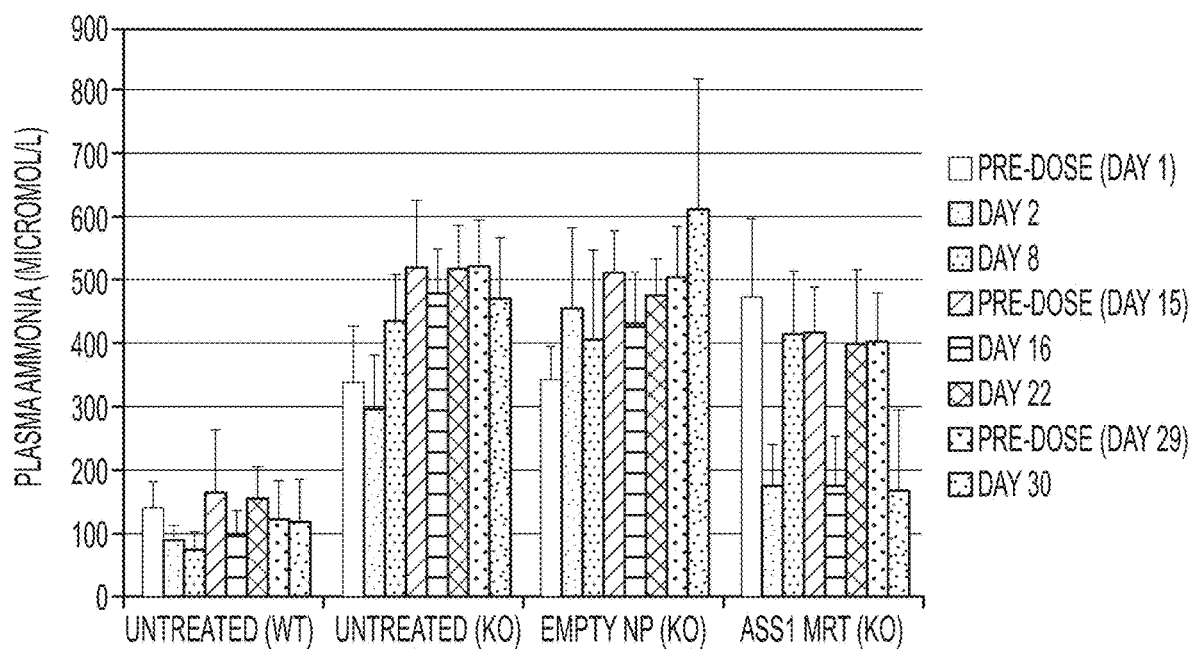
FIG. 11 depicts plasma ammonia levels in AAS1 knock-out mice administered 1.0 mg/kg of ASS1 mRNA-loaded lipid nanoparticles every 14 days for 30 days.

Male CD-1 mice were administered a single dose of 1.0 mg/kg of lipid nanoparticles (ASS1 mRNA-loaded cKK-E12-based lipid nanoparticle) intravenously, or untreated (i.e., control), as described above in Example 2. The mice were sacrificed and the organs were collected 24 hours post-administration. Human argininosuccinate synthetase (ASS1) protein levels in the liver were measured by ELISA. These data demonstrate increased levels of ASS1 protein were detected relative to the control and that the protein produced resulted from ASS1 mRNA delivered intravenously (FIG. 10).

Example 5

Plasma Ammonia Levels Following Treatment with ASS1 mRNA-Loaded Lipid Nanoparticles This example demonstrates that administration of ASS1 mRNA results in successful reduction of plasma ammonia levels.

ASS1 knockout mice were administered 1.0 mg/kg of ASS1 mRNA lipid nanoparticles (ASS1 mRNA-loaded cKK-E12-based lipid nanoparticle) or empty lipid nanoparticles once every 14 days for 30 days as described above in Example 2. Mice which were administered empty lipid nanoparticles served as the vehicle control. Additional controls included untreated wild-type mice and untreated ASS1 knockout mice. Prior to each dose on days 1, 15 and 29, plasma samples were collected (i.e., pre-dose). Plasma samples were also collected within 24 hours following each dose on days 2, 16 and 30. Additional plasma samples were collected on days 8 and 22. Plasma ammonia levels were quantified in all samples and demonstrated that plasma ammonia levels were reproducibly reduced for at least 24 hours following treatment to levels near those observed in wild-type mice.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating Argininosuccinate Synthetase Deficiency (ASD), the method comprising
   administering intravenously to a subject with the ASD a composition comprising an mRNA-loaded liposome at an effective dose and administration interval to treat the ASD;
   wherein the administering results in reduced ammonia levels in a blood sample from the treated subject as compared to a baseline ammonia level before treatment;
   wherein the mRNA encodes an human argininosuccinate synthetase (ASS1) and comprises a nucleotide sequence at least 90% identical to SEQ ID NO: 3
```
AUGAGCAGCAAGGGCAGCGUGGUGCUGGCCUACAGCGGCGGCCUGGACACC
AGCUGCAUCCUGGUGUGGCUGAAGGAGCAGGGCUACGACGUGAUCGCCUAC
CUGGCCAACAUCGGCCAGAAGGAGGACUUCGAGGAGGCCCGCAAGAAGGCC
CUGAAGCUGGGCGCCAAGAAGGUGUUCAUCGAGGACGUGAGCCGCGAGUUC
GUGGAGGAGUUCAUCUGGCCCGCCAUCCAGAGCAGCGCCCUGUACGAGGAC
CGCUACCUGCUGGGCACCAGCCUGGCCCGCCCCUGCAUCGCCCGCAAGCAG
GUGGAGAUCGCCCAGCGCGAGGGCGCCAAGUACGUGAGCCACGGCGCCACC
GGCAAGGGCAACGACCAGGUGCGCUUCGAGCUGAGCUGCUACAGCCUGGCC
CCCCAGAUCAAGGUGAUCGCCCCCUGGCGCAUGCCCGAGUUCUACAACCGC
UUCAAGGGCCGCAACGACCUGAUGGAGUACGCCAAGCAGCACGGCAUCCCC
AUCCCCGUGACCCCCAAGAACCCCUGGAGCAUGGACGAGAACCUGAUGCAC
AUCAGCUACGAGGCCGGCAUCCUGGAGAACCCCAAGAACCAGGCCCCCCCC
GGCCUGUACACCAAGACCCAGGACCCCGCCAAGGCCCCCAACACCCCCGAC
AUCCUGGAGAUCGAGUUCAAGAAGGGCGUGCCCGUGAAGGUGACCAACGUG
AAGGACGGCACCACCCACCAGACCAGCCUGGAGCUGUUCAUGUACCUGAAC
GAGGUGGCCGGCAAGCACGGCGUGGGCCGCAUCGACAUCGUGGAGAACCGC
UUCAUCGGCAUGAAGAGCCGCGGCAUCUACGAGACCCCCGCCGGCACCAUC
CUGUACCACGCCCACCUGGACAUCGAGGCCUUCACCAUGGACCGCGAGGUG
CGCAAGAUCAAGCAGGGCCUGGGCCUGAAGUUCGCCGAGCUGGGUGUACACC
```

GGCUUCUGGCACAGCCCCGAGUGCGAGUUCGUGCGCCACUGCAUCGCCAAG

AGCCAGGAGCGCGUGGAGGGCAAGGUGCAGGUGAGCGUGCUGAAGGGCCAG

GUGUACAUCCUGGGCCGCGAGAGCCCCCUGAGCCUGUACAACGAGGAGCUG

GUGAGCAUGAACGUGCAGGGCGACUACGAGCCCACCGACGCCACCGGCUUC

AUCAACAUCAACAGCCUGCGCCUGAAGGAGUACCACCGCCUGCAGAGCAAG

GUGACCGCCAAGUGA;

wherein the liposome has a diameter less than about 100 nm; and wherein the liposome comprises one or more cationic lipids, one or more non-cationic lipids, one or more cholesterol-based lipids and one or more PEG-modified lipids.

2. The method of claim 1, wherein the one or more cationic lipids comprise a cationic lipid selected from the group consisting of C12-200, MC3, DLinDMA, DLinkC2DMA, cKK-E12, ICE (Imidazol-based), HGT5000, HGT5001, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combination thereof.

3. The method of claim 1, wherein the one or more cholesterol-based lipids are at least one of cholesterol and PEGylated cholesterol.

4. The method of claim 1, wherein the one or more cationic lipids constitutes about 30-50% of the liposome by weight.

5. The method of claim 1, wherein the ratio of the one or more cationic lipids: the one or more non-cationic lipids: the one or more cholesterol-based lipids: the one or more PEG-modified lipids is approximately 40:30:25:5 by molar ratio.

6. The method of claim 1, wherein the liposome comprises a combination selected from:
cKK-E12, DOPE, cholesterol and DMG-PEG2K;
C12-200, DOPE, cholesterol and DMG-PEG2K;
HGT4003, DOPE, cholesterol and DMG-PEG2K; or ICE, DOPE, cholesterol and DMG-PEG2K.

7. The method of claim 1, wherein the effective dose ranges from about 0.01 to 5.0 mg/kg body weight.

8. The method of claim 1, wherein the composition is administered once a week.

9. The method of claim 1, wherein the administering of the composition results in a reduced citrulline level in the subject as compared to a baseline citrulline level before the treatment.

10. The method of claim 1, wherein the mRNA is codon optimized.

11. The method of claim 1, wherein the mRNA comprises one or more modified nucleotides.

12. The method of claim 1, wherein the mRNA is unmodified.

13. The method of claim 1, wherein the mRNA comprises a nucleotide sequence identical to

SEQ ID NO: 3
AUGAGCAGCAAGGGCAGCGUGGUGCUGGCCUACAGCGGCGGCCUGGACACC

AGCUGCAUCCUGGUGUGGCUGAAGGAGCAGGGCUACGACGUGAUCGCCUAC

CUGGCCAACAUCGGCCAGAAGGAGGACUUCGAGGAGGCCCGCAAGAAGGCC

CUGAAGCUGGGCGCCAAGAAGGUGUUCAUCGAGGACGUGAGCCGCGAGUUC

GUGGAGGAGUUCAUCUGGCCCGCCAUCCAGAGCAGCGCCCUGUACGAGGAC

CGCUACCUGCUGGGCACCAGCCUGGCCCGCCCCUGCAUCGCCCGCAAGCAG

GUGGAGAUCGCCCAGCGCGAGGGCGCCAAGUACGUGAGCCACGGCGCCACC

GGCAAGGGCAACGACCAGGUGCGCUUCGAGCUGAGCUGCUACAGCCUGGCC

CCCCAGAUCAAGGUGAUCGCCCCCUGGCGCAUGCCCGAGUUCUACAACCGC

UUCAAGGGCCGCAACGACCUGAUGGAGUACGCCAAGCAGCACGGCAUCCCC

AUCCCCGUGACCCCCAAGAACCCCUGGAGCAUGGACGAGAACCUGAUGCAC

AUCAGCUACGAGGCCGGCAUCCUGGAGAACCCCAAGAACCAGGCCCCCCCC

GGCCUGUACACCAAGACCCAGGACCCCGCCAAGGCCCCCAACACCCCCGAC

AUCCUGGAGAUCGAGUUCAAGAAGGGCGUGCCCGUGAAGGUGACCAACGUG

AAGGACGGCACCACCCACCAGACCAGCCUGGAGCUGUUCAUGUACCUGAAC

GAGGUGGCCGGCAAGCACGGCGUGGGCCGCAUCGACAUCGUGGAGAACCGC

UUCAUCGCCAUGAAGAGCCGCGGCAUCUACGAGACCCCCGCCGGCACCAUC

CUGUACCACGCCCACCUGGACAUCGAGGCCUUCACCAUGGACCGCGAGGUG

CGCAAGAUCAAGCAGCGCCUGGGCCUGAAGUUCGCCGAGCUGGUGUACACC

GGCUUCUGGCACAGCCCCGAGUGCGAGUUCGUGCGCCACUGCAUCGCCAAG

AGCCAGGAGCGCGUGGAGGGCAACGUGCAGGUGAGCGUGCUGAAGGGCCAG

GUGUACAUCCUGGGCCGCGAGAGCCCCCUGAGCCUGUACAACGAGGAGCUG

GUGAGCAUGAACGUGCAGGGCGACUACGAGCCCACCGACGCCACCGGCUUC

AUCAACAUCAACAGCCUGCGCCUGAAGGAGUACCACCGCCUGCAGAGCAAG

GUGACCGCCAAGUGA.

14. A method of treating Argininosuccinate Synthetase Deficiency (ASD), the method comprising administering intravenously to a subject with the ASD a composition comprising an mRNA molecule encoding an human argininosuccinate synthetase (ASS1) encapsulated in a liposome at an effective dose and an administration interval such that the administering of the composition results in reduced ammonia levels in a blood sample from the treated subject as compared to a baseline ammonia level before treatment, wherein the liposome has a diameter of less than about 100 nm, and wherein the liposome comprises cKK-E12:

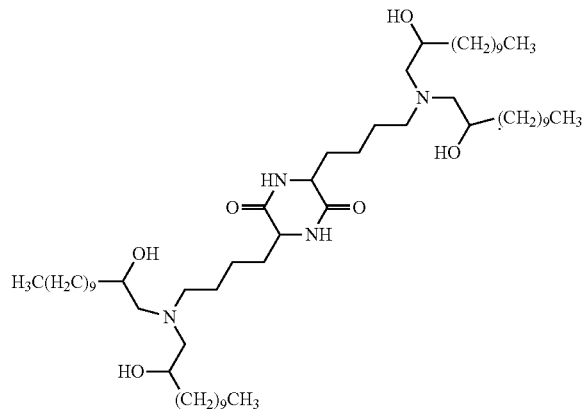

15. The method of claim 14, wherein the mRNA comprises a nucleotide sequence at least 90% identical to

```
                                              SEQ ID NO: 3
AUGAGCAGCAAGGGCAGCGUGGUGCUGGCCUACAGCGGCGGCCUGGACACC

AGCUGCAUCCUGGUGUGGCUGAAGGAGCAGGGCUACGACGUGAUCGCCUAC

CUGGCCAACAUCGGCCAGAAGGAGGACUUCGAGGAGGCCCGCAAGAAGGCC

CUGAAGCUGGGCGCCAAGAAGGUGUUCAUCGAGGACGUGAGCCGCGAGUUC

GUGGAGGAGUUCAUCUGGCCCGCCAUCCAGAGCAGCGCCCUGUACGAGGAC

CGCUACCUGCUGGGCACCAGCCUGGCCCGCCCCUGCAUCGCCCGCAAGCAG

GUGGAGAUCGCCCAGCGCGAGGGCGCCAAGUACGUGAGCCACGGCGCCACC

GGCAAGGGCAACGACCAGGUGCGCUUCGAGCUGAGCUGCUACAGCCUGGCC

CCCCAGAUCAAGGUGAUCGCCCCCUGGCGCAUGCCCGAGUUCUACAACCGC

UUCAAGGGCCGCAACGACCUGAUGGAGUACGCCAAGCAGCACGGCAUCCCC

AUCCCCGUGACCCCCAAGAACCCCUGGAGCAUGGACGAGAACCUGAUGCAC

AUCAGCUACGAGGCCGGCAUCCUGGAGAACCCCAAGAACCAGGCCCCCCCC

GGCCUGUACACCAAGACCCAGGACCCCGCCAAGGCCCCCAACACCCCCGAC

AUCCUGGAGAUCGAGUUCAAGAAGGGCGUGCCCGUGAAGGUGACCAACGUG

AAGGACGGCACCACCCACCAGACCAGCCUGGAGCUGUUCAUGUACCUGAAC

GAGGUGGCCGGCAAGCACGGCGUGGGCCGCAUCGACAUCGUGGAGAACCGC

UUCAUCGCCAUGAAGAGCCGCGGCAUCUACGAGACCCCCGCCGGCACCAUC

CUGUACCACGCCCACCUGGACAUCGAGGCCUUCACCAUGGACCGCGAGGUG

CGCAAGAUCAAGCAGCGCCUGGGCCUGAAGUUCGCCGAGCUGGUGUACACC

GGCUUCUGGCACAGCCCCGAGUGCGAGUUCGUGCGCCACUGCAUCGCCAAG
```

```
AGCCAGGAGCGCGUGGAGGGCAACGUGCAGGUGAGCGUGCUGAAGGGCCAG

GUGUACAUCCUGGGCCGCGAGAGCCCCCUGAGCCUGUACAACGAGGAGCUG

GUGAGCAUGAACGUGCAGGGCGACUACGAGCCCACCGACGCCACCGGCUUC

AUCAACAUCAACAGCCUGCGCCUGAAGGAGUACCACCGCCUGCAGAGCAAG

GUGACCGCCAAGUGA.
```

16. The method of claim 14, wherein the mRNA comprises a nucleotide sequence identical to

```
                                              SEQ ID NO: 3
AUGAGCAGCAAGGGCAGCGUGGUGCUGGCCUACAGCGGCGGCCUGGACACC

AGCUGCAUCCUGGUGUGGCUGAAGGAGCAGGGCUACGACGUGAUCGCCUAC

CUGGCCAACAUCGGCCAGAAGGAGGACUUCGAGGAGGCCCGCAAGAAGGCC

CUGAAGCUGGGCGCCAAGAAGGUGUUCAUCGAGGACGUGAGCCGCGAGUUC

GUGGAGGAGUUCAUCUGGCCCGCCAUCCAGAGCAGCGCCCUGUACGAGGAC

CGCUACCUGCUGGGCACCAGCCUGGCCCGCCCCUGCAUCGCCCGCAAGCAG

GUGGAGAUCGCCCAGCGCGAGGGCGCCAAGUACGUGAGCCACGGCGCCACC

GGCAAGGGCAACGACCAGGUGCGCUUCGAGCUGAGCUGCUACAGCCUGGCC

CCCCAGAUCAAGGUGAUCGCCCCCUGGCGCAUGCCCGAGUUCUACAACCGC

UUCAAGGGCCGCAACGACCUGAUGGAGUACGCCAAGCAGCACGGCAUCCCC

AUCCCCGUGACCCCCAAGAACCCCUGGAGCAUGGACGAGAACCUGAUGCAC

AUCAGCUACGAGGCCGGCAUCCUGGAGAACCCCAAGAACCAGGCCCCCCCC

GGCCUGUACACCAAGACCCAGGACCCCGCCAAGGCCCCCAACACCCCCGAC

AUCCUGGAGAUCGAGUUCAAGAAGGGCGUGCCCGUGAAGGUGACCAACGUG

AAGGACGGCACCACCCACCAGACCAGCCUGGAGCUGUUCAUGUACCUGAAC

GAGGUGGCCGGCAAGCACGGCGUGGGCCGCAUCGACAUCGUGGAGAACCGC

UUCAUCGCCAUGAAGAGCCGCGGCAUCUACGAGACCCCCGCCGGCACCAUC

CUGUACCACGCCCACCUGGACAUCGAGGCCUUCACCAUGGACCGCGAGGUG

CGCAAGAUCAAGCAGCGCCUGGGCCUGAAGUUCGCCGAGCUGGUGUACACC

GGCUUCUGGCACAGCCCCGAGUGCGAGUUCGUGCGCCACUGCAUCGCCAAG

AGCCAGGAGCGCGUGGAGGGCAACGUGCAGGUGAGCGUGCUGAAGGGCCAG

GUGUACAUCCUGGGCCGCGAGAGCCCCCUGAGCCUGUACAACGAGGAGCUG

GUGAGCAUGAACGUGCAGGGCGACUACGAGCCCACCGACGCCACCGGCUUC

AUCAACAUCAACAGCCUGCGCCUGAAGGAGUACCACCGCCUGCAGAGCAAG

GUGACCGCCAAGUGA.
```

\* \* \* \* \*